(12) United States Patent
Stahn

(10) Patent No.: US 9,359,427 B2
(45) Date of Patent: Jun. 7, 2016

(54) METHODS FOR CULTURING HUMAN MYELOID LEUKAEMIA CELLS AND CELLS DERIVED THEREFROM

(75) Inventor: Rainer Stahn, Berlin (DE)

(73) Assignee: Glycotope GmbH, Berlin (DE)

( * ) Notice: Subject to any disclaimer, the term of this patent is extended or adjusted under 35 U.S.C. 154(b) by 348 days.

(21) Appl. No.: 13/995,730

(22) PCT Filed: Dec. 21, 2011

(86) PCT No.: PCT/EP2011/073702
§ 371 (c)(1),
(2), (4) Date: Aug. 28, 2013

(87) PCT Pub. No.: WO2012/085162
PCT Pub. Date: Jun. 28, 2012

(65) Prior Publication Data
US 2013/0330768 A1    Dec. 12, 2013

Related U.S. Application Data

(60) Provisional application No. 61/425,743, filed on Dec. 21, 2010.

(51) Int. Cl.
*C12P 21/02*    (2006.01)
*C07K 16/00*    (2006.01)
*C12N 5/09*    (2010.01)

(52) U.S. Cl.
CPC .............. *C07K 16/00* (2013.01); *C12N 5/0694* (2013.01); *C12N 2511/00* (2013.01); *C12N 2521/00* (2013.01)

(58) Field of Classification Search
None
See application file for complete search history.

(56) References Cited

FOREIGN PATENT DOCUMENTS

WO    2008/028686 A2    3/2008

OTHER PUBLICATIONS

Biostat-B Manual (2014) pp. 1-24.*
Berdugo, Claudia, "Cell Damage Mechanisms and Stress Response in ANimal Cell Culture," Dissertation, Graduate Program in Chemical and Biomolecular Engineering, The Ohio State University, 321 pages, (2010).
Hicks, Martin G. et al., "Glyco-Bioinformatics, Bits 'n' Bytes of Sugars," Proceedings of the International Beilstein Symposium, retrieved online at: http://www.beilstein-institut.de/glycobioinf2009/Proceedings/GlycoBioinformatics_2009_Proceedings.pdf, 180 pages, (2009).
Stiens, Lars R. et al., "Development of Serum-Free Bioreactor Production of Recombinant Human Thyroid Stimulating Hormone Receptor," Biotechnol. Prog., vol. 16:703-709 (2000).
International Preliminary Report on Patentability for Application No. PCT/EP2011/073702, 6 pages, dated Jun. 25, 2013.
International Search Report for Application No. PCT/EP2011/073702, 8 pages, dated May 10, 2012.
Andersen, Dana C. et al., "Production technologies for monoclonal antibodies and their fragments," Current Opinion in Biotechnology, vol. 15:456-462 (2004).
Dalm, Marcella C.F. et al., "Effect of Feed and Bleed Rate on Hybridoma Cells in an Acoustic Perfusion Bioreactor: Part I. Cell Density, Viability, and Cell-Cycle Distribution," Biotechnology and Bioengineering, vol. 88(5):547-557 (2004).
Dalm, Marcella C.F. et al., "Effect of Feed and Bleed Rate on Hybridoma Cells in an Acoustic Perfusion Bioreactor: Metabolic Analysis," Biotechnol. Prog., vol. 23:560-569 (2007).
Godoy-Silva, Ruben et al., "Physiological Responses of CHO Cells to Repetitive Hydrodynamic Stress," Biotechnology and Bioengineering, vol. 103(6):1103-1116 (2009).
Kunkel, Jeremy P. et al., "Dissolved oxygen concentration in serum-free continuous culture affects N-linked glycosylation of a monoclonal antibody," Journal of Biotechnology, vol. 62:55-71 (1998).
Lipscomb, Matthew L. et al., "Effect of Production Method and Gene Amplification on the Glycosylation Pattern of a Secreted Reporter Protein in CHO Cells," Biotechnol. Prog., vol. 40-49 (2005).
Marks, David M., "Equipment design considerations for large scale cell cuture," Cytotechnology, vol. 42:21-33 (2003).
Morrow, K. John Jr., Advances in antibody manufacturing using mammalian cells, Biotechnology Annual Review, vol. 13:95-113 (2007).
Motobu, Maki et al., "Effect of Shear Stress on Recombinant Chinese Hamster Ovary Cells," Journal of Fermentation Bioengineering, vol. 85(2):190-195 (1998).
Muthing, Johannes et al., "Effects of Buffering Conditions and Culture pH on Production Rates and Glycosylation of Clinical Phase I Anti-melanoma Mouse IgG3 Monoclonal Antibody R24," Biotechnology and Bioengineering, vol. 83 (3):321-334 (2003).
Senger, Ryan S. et al., "Effect of Shear Stress on Intrinsic CHO Cuture State and Glycosylation of Recombinant Tissue-Type Plasminogen Activator Protein," Biotechnol. Prog., vol. 19:1199-1209 (2003).
Shukla, Abhinav A. et al., "Recent advances in large-scale production of monoclonal antibodies and related proteins," Trends in Biotechnology, vol. 28(5):253-261 (2010).
Tachibana, Hirofumi et al., "Changes of monosaccharide availability of human hybridoma lead to alteration of biological properties of human monoclonal antibody," Cytotechnology, vol. 16:151-157 (1994).
Ahn, Woo Suk et al., "Effect of Culture Temperature on Erythropoietin Production and Glycosylation in a Perfusion Culture of Recombinant CHO Cells," Biotechnology and Bioengineering, vol. 101(6):1234-1244 (2008).

* cited by examiner

*Primary Examiner* — Jim Ketter
(74) *Attorney, Agent, or Firm* — Nelson Mullins Riley & Scarborough LLP; James E. Remillard, Esq.; Jill Gorny Sloper, Esq.

(57) ABSTRACT

The present invention pertains to a method for culturing a suspension of immortalized human blood cells, preferably cells of myeloid leukaemia origin or cells derived therefrom, wherein said method provides a high productivity, a high cell viability and growth rate and a high batch-to-batch consistency, and can be scaled up without altering these parameters.

26 Claims, 11 Drawing Sheets

A

B

Fig. 1 - continued
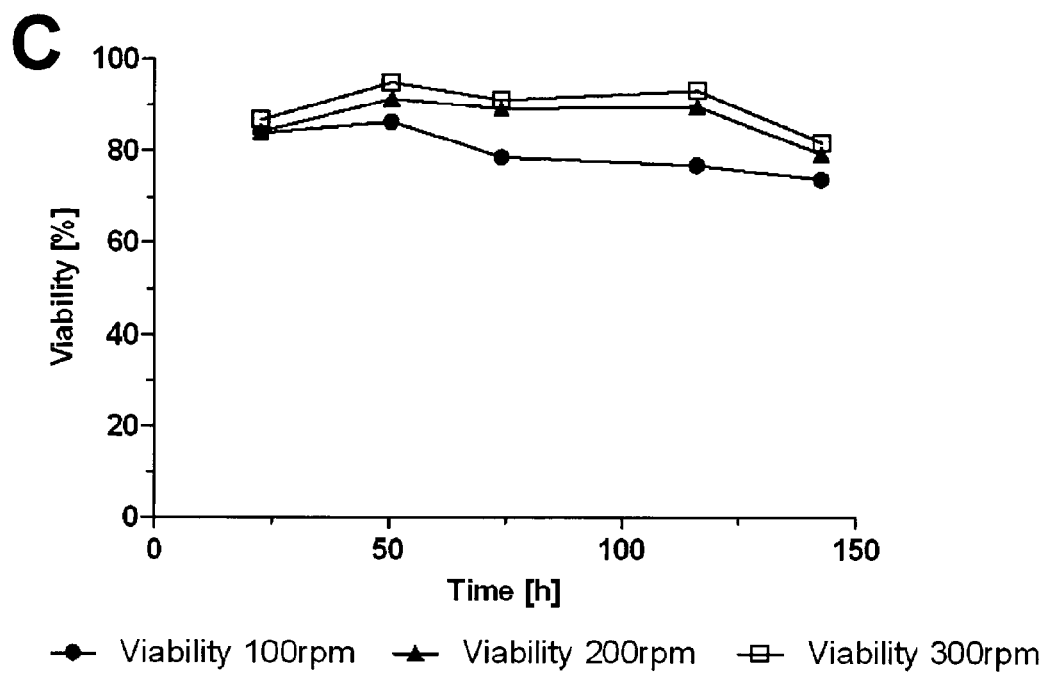

A

B

Fig. 2 - continued
C
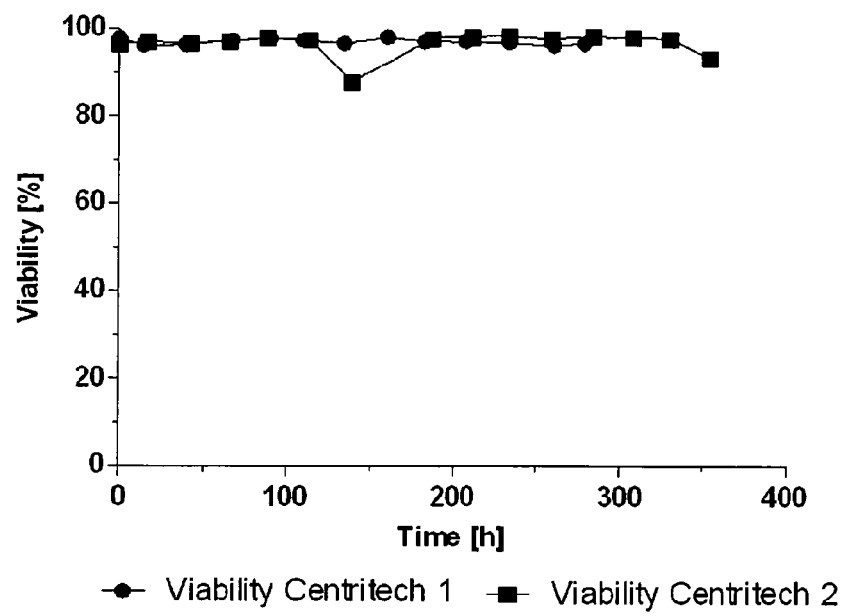
D
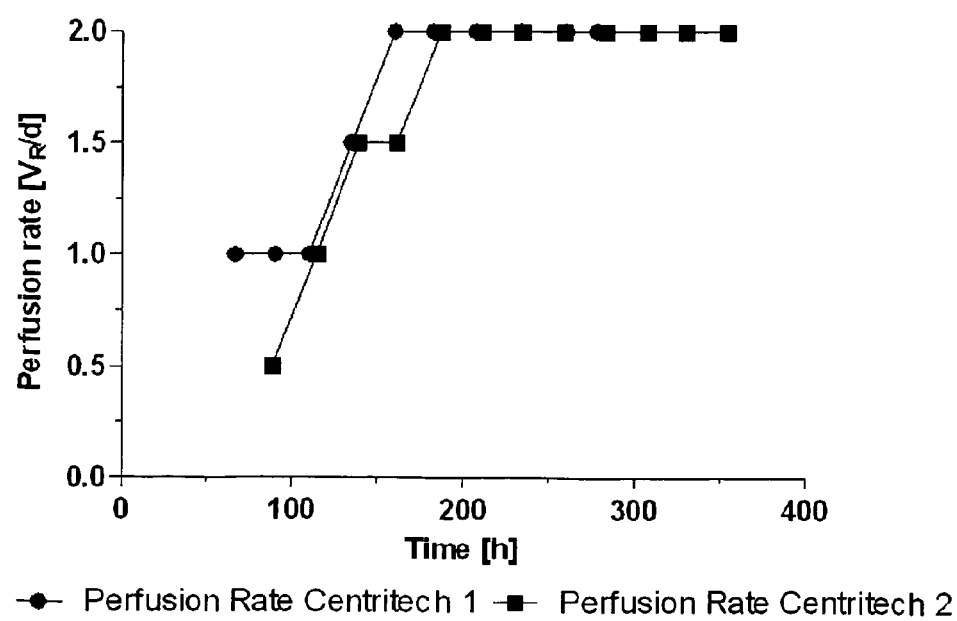

Fig. 2 - continued
E
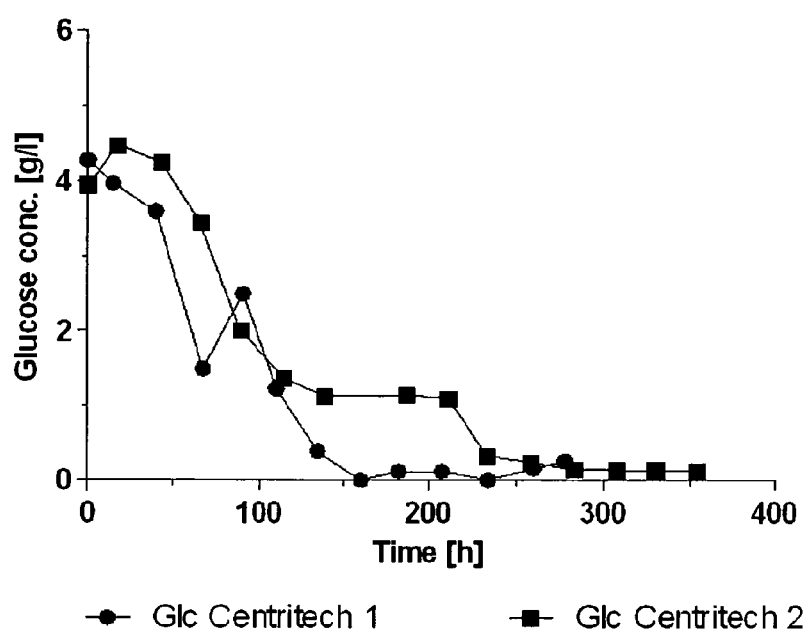

A

B

Fig. 3 - continued
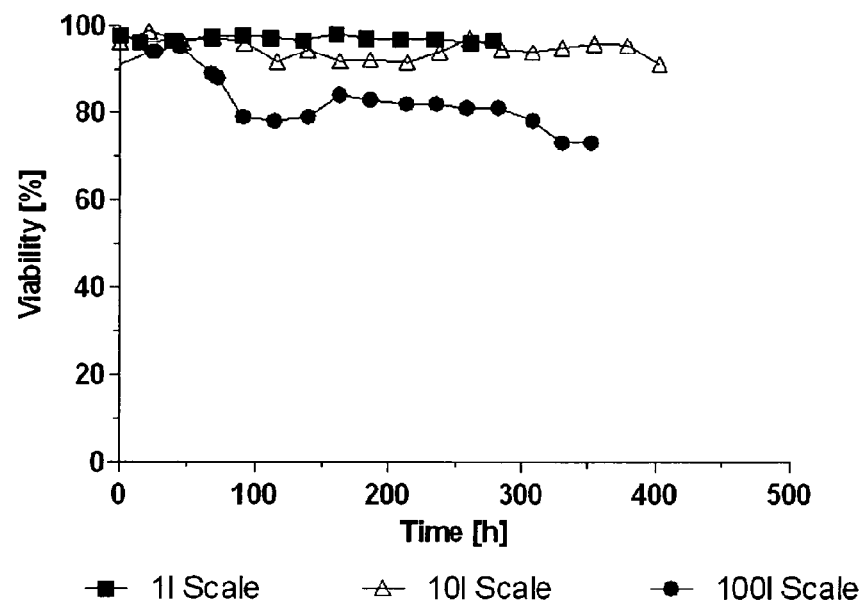
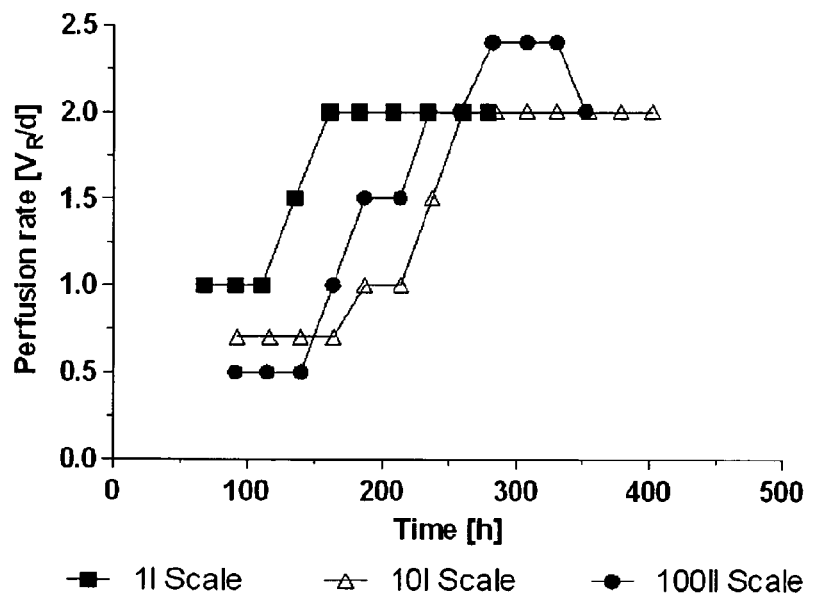

Fig. 3 - continued
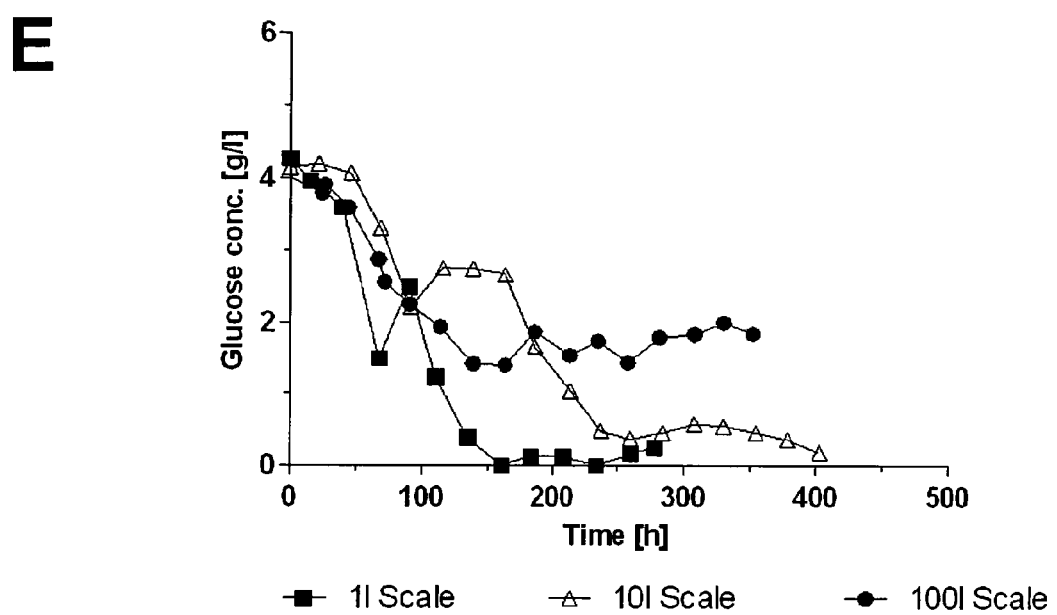

Fig. 4 - continued
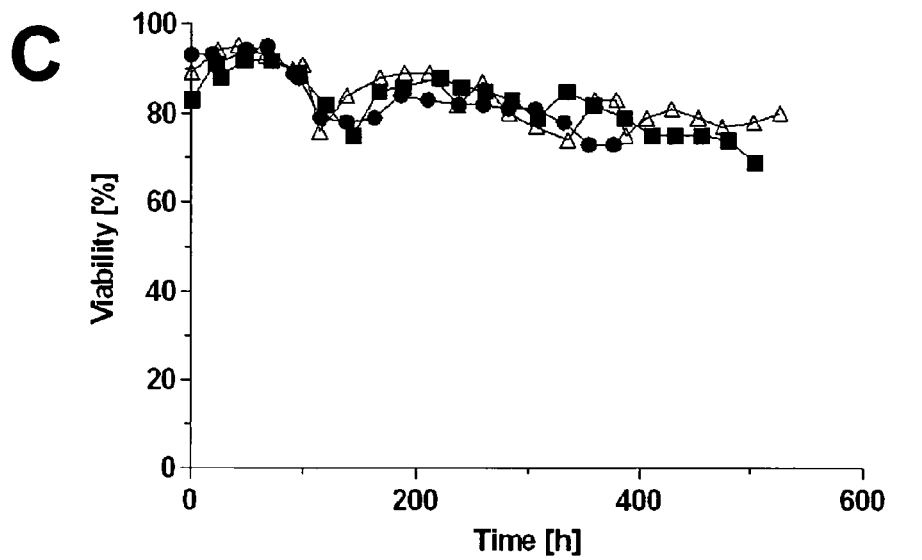
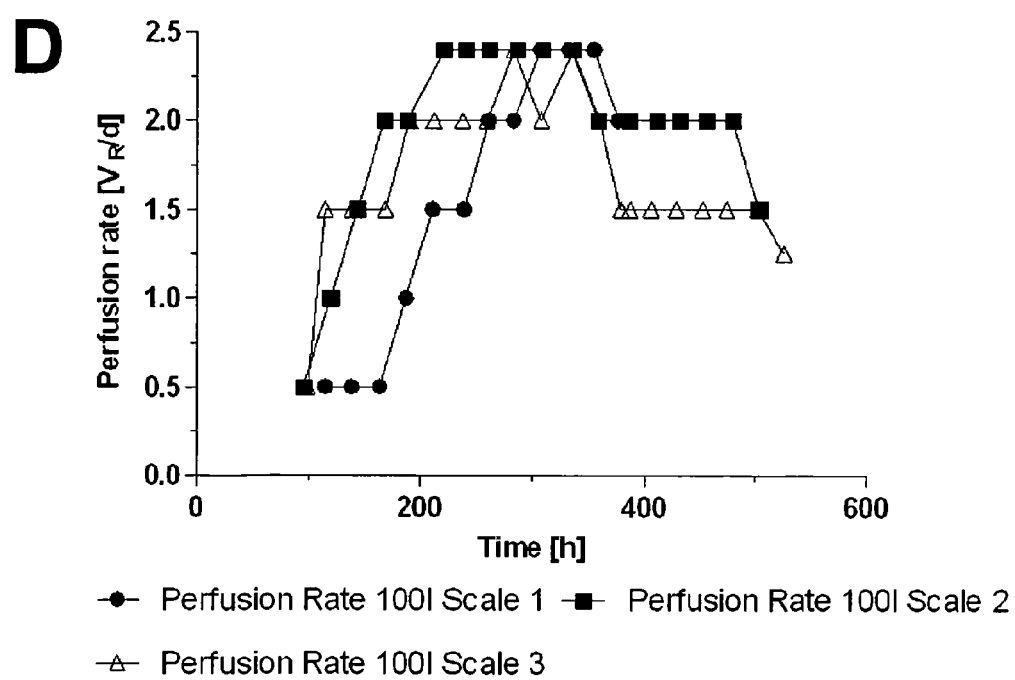

Fig. 4 - continued
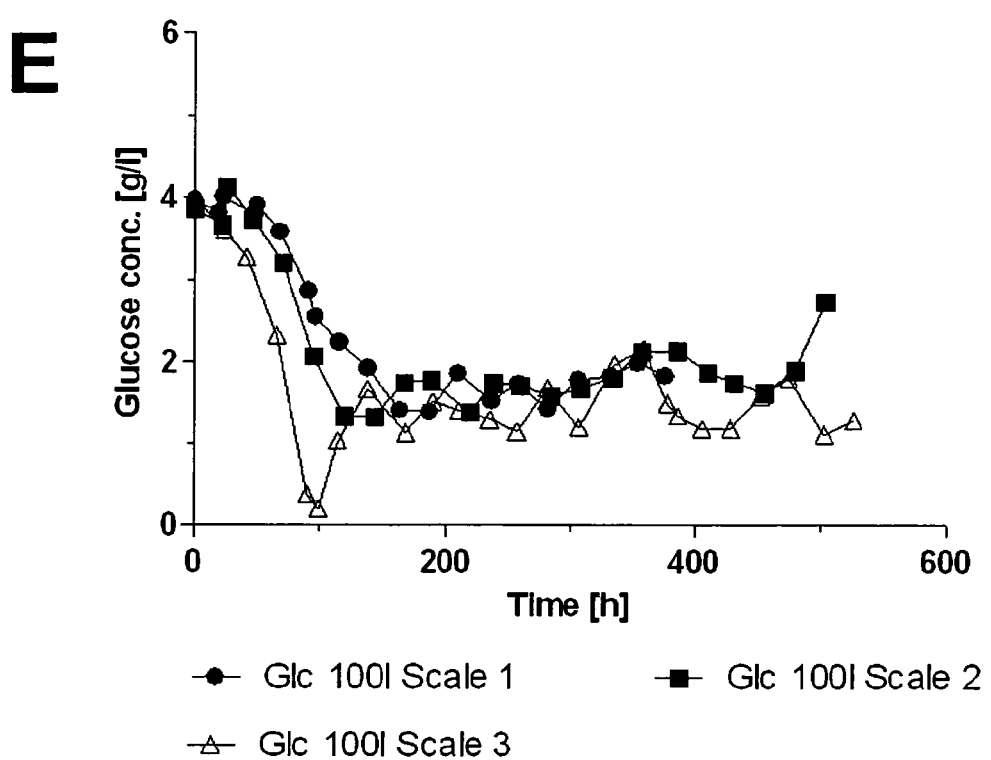

METHODS FOR CULTURING HUMAN MYELOID LEUKAEMIA CELLS AND CELLS DERIVED THEREFROM

RELATED APPLICATIONS

This application is a 35 U.S.C. 371 national stage filing of International Application No. PCT/EP2011/073702, filed on Dec. 21, 2011, which claims priority to U.S. Provisional Application No. 61/425,743, filed on Dec. 21, 2010. The contents of the aforementioned applications are hereby incorporated by reference.

FIELD OF THE INVENTION

The present invention relates to a method for culturing human immortalized blood cells, preferably cells of human myeloid leukemia origin or cells derived therefrom, to a method for the recombinant production of a product of interest and to a method for altering the volume scale of the fermentation for producing a product of interest.

BACKGROUND OF THE INVENTION

For producing a product of interest such as in particular a protein, recombinant techniques are widely applied. The product of interest is expressed in a suitable host cell and the expressed product is obtained e.g. from the cells and/or the cell culture medium.

The basic idea of fermentation is to maintain cells under optimal conditions for a period of time in different scales in order to produce high amounts of the desired product. Fermentation is common for procaryotes (e.g. *Escherichia coli*), yeast (e.g. *Pichia pastoris*) and mammalian cells (e.g. rodent cell lines such as Chinese hamster ovary cells (CHO), mouse myeloma cells (NSO; SP2/0) or human cell lines). Beside an optimized culture media, a well controlled fermentation process is the basis for a production process in mammalian cell culture. Depending on the production cell line, cells are either grown in suspension culture or on a carrier matrix for anchorage-dependent cell culture. Small scale cell culture is performed using a relative low level of instrumentation. For suspension culture roller bottles and spinner flasks are e.g. suitable. Small scale cell culture is usually operated in a humidified carbon dioxide incubator. As gas transfer in a carbon dioxide incubator is based upon passive diffusion, gas transfer limitations can occur. The technique of fermentation for the production of pharmaceutical products is covered extensively in the literature as numerous reviews are available e.g. [Andersen and Reilly 2004], [Shukla and Thömmes 2010], [Marks 2003] and [Morrow 2007]. Regarding the operation of cell culture fermentation, there are four different basic strategies for bioreactors, which have been described in the literature: batch, fed-batch, continuous fermentation without cell retention and continuous fermentation with cell retention (perfusion). As perfusion does include a cell retention, the only way of removing cells during cultivation is the usage of a bleed (removal of cell suspension).

Fermentation parameters are characteristic for a production process. Changing those parameters may increase or decrease the product yield. Inside the bioreactor temperature, dissolved oxygen and pH-value are basic parameters to be controlled. Strategies for optimization base upon adjustment of those parameters. Some parameters, which are suitable for optimization include but are not limited to the temperature used during fermentation, the used oxygen level, the cell retention and the composition of the used media.

Furthermore, also the chosen aeration/sparging can be an important feature for the culturing process. Cells growing in cell culture require oxygen for efficient growth. In small cultivation volumes the amount of oxygen that reaches the cells by diffusion via the surface of the cultivation medium is generally sufficient. However as the cultivation volume increases, the specific addition of oxygen becomes necessary. This is normally achieved by sparging, so that bubbles of the gas or gases to be supplied to the cell culture are introduced. When larger vessel sizes are required, homogeneous gas supply becomes more and more of a concern. However the gas supply cannot be arbitrarily increased because most mammalian cells tend to be sensitive to shear forces created by the bubbles. Said bubbles carry attached cells to the surface, where the bubbles rupture under formation of high hydrodynamic stress, thereby killing the attached cells. These lethal effects can reduce the cell viability and hence the productivity of a cell culture. Bubble-free gas supply systems (e.g. membranes) that may prove useful in smaller cultures are not practical for use in larger cultures during scale up. Reasons for this are for example the high costs associated with the use of membranes or technical limitations in the large vessels.

Furthermore, in order to achieve a homogenous cell culture, the suspension is usually mixed by agitation. This can be achieved e.g. by impeller agitation and gas sparging. For agitation usually a stirrer is used. However there are also limitations to agitation. Cells usually tend to be sensitive to the shear forces induced by agitation, for example stirring. Therefore, the potential for ensuring homogeneity by agitation is limited.

Regarding mixing, there are two specific problems: (i) the addition of base solution and feed solution and (ii) carbon dioxide accumulation. Concentration variations of substrate levels but also oxygen gradients can occur. They are more common in large vessels than in small vessels. Uneven distribution increases with vessel size and becomes more and more critical. The main problem of mixing is the trade-off between inhomogeneities and shear forces. To ensure sufficient mixing and non-damaging shear stress is an intriguing challenge. Both mixing and shear stress can lead to cell death by different means. Insufficient mixing can e.g. lead to clumping or oxygen limitation while shear stress can lyse cells.

Hydrodynamic stress based on shear forces is a major cell culture issue. Generally, damage by shear forces is to a very high extent cell line dependent. Additionally, as peak cell densities of fed-batch or perfusion processes increase due to process and medium optimisation there is an additional demand for mixing as the viscosity increases. Hydrodynamic stress in a stirred tank bioreactor is a non-homogeneous phenomenon. In impeller regions, which account for only about 10% of total volume, up to 70% of energy is dissipated. Consequently, also shear forces are much higher in those regions close to the impeller which may cause lethal or non-lethal damaging effects on the cells. Not only can hydrodynamic stress lyse cells; it may also influence cells on a sublytic level, which is currently not well understood.

These factors contribute to the fact that culturing conditions that might be suitable for small-scale cultures cannot be easily transferred to large scale cultures. The outcome of protein production in large-scale cultures is often considerably different from that of small-scale cultures. During large scale production, very often the productivity and/or the quality of the produced protein (e.g. the glycosylation structures in case the glycoprotein is recombinantly produced) is decreased. All together the scale up remains a major issue in mammalian cell culture. Although a lot of literature is available for scale up procedures regarding scale up concepts and considerations, scale up remains a challenge and measures suitable for one specific cell line, can very often not be transferred to a different cell line.

When producing a glycosylated product of interest, such as e.g. an antibody that is to be used in therapy, it is desirous to obtain a "human" or "humanised" glycosylation structure. Several techniques and host cells are available for that purpose. Immortilized human blood cells and cell lines derived therefrom were found suitable for recombinantly producing glycosylated products having a human glycosylation pattern. Respective cell lines are e.g. described in WO 2008/028686. Product glycosylation is a complex post-translational modification which may be affected by a lot of different parameters. These parameters can be of physical, chemical or thermodynamic nature. As these parameters can be affected during fermentation, it is very important to develop a fermentation process that allows to produce a product with a constant, i.e. homogenous glycosylation pattern. There are several reports to be found in the literature. It is e.g. reported that shear force, glucose availability, oxygen saturation, pH, temperature and other process conditions may affect glycosylation [Senger and Karim 2003] [Godoy-Silva et al. 2009] [Tachibana et al. 1994] [Kunkel et al. 1998] [Müthing et al. 2003] [Ahn et al. 2008] [Lipscomb et al. 2005].

It is an object of the present invention to provide a method for culturing cells, in particular immortalized human blood cells, which allows to produce a product of interest with acceptable yield and good quality also when using different fermentation volumes (scales).

SUMMARY OF THE INVENTION

The present invention is inter alia based on the surprising finding that an increase in the agitation of the cell culture results despite an associated increase in the shear forces in considerably improved culturing conditions which allow the production of a product of interest with good yield and quality also during scale up. This is an important advantage in particular when producing a product of interest such as a glycoprotein for therapeutic uses. For such applications, changes in the product quality when using different fermenter volumes are unacceptable in the GMP process, respectively increase the necessary efforts for obtaining the approval from the regulatory authorities. It was in particular found that the cell density and the cell viability can be improved with the culturing method according to the present invention. The nutrient transport in the cell culture medium is improved and the aeration rate can be reduced which reduces the damage of the cells due to bubble development. Furthermore, it was found that the culturing process is improved if the size and/or the amount of bubbles that develop due to aeration is kept at a minimum when culturing immortalized human blood cells, preferably cells of human myeloid leukaemia origin.

According to a first aspect, a method for culturing a suspension of immortalized human blood cells, preferably cells of human myeloid leukaemia origin or cells derived therefrom is provided, wherein said method has one or more of the following characteristics:

a) said suspension is agitated such that the resulting specific power input is at least 0.005 W/kg, preferably at least 0.01, 0.015, 0.02, 0.025, 0.03, 0.04, 0.05, 0.075 or 0.1 W/kg, more preferred in a range of 0.015 to 0.03, more preferred 0.018 to 0.025 W/Kg, b) said suspension is agitated with an intensity that is suitable for allowing an exclusive flow gas supply of said suspension, c) said suspension is agitated such that the resulting shear force is at least 0.1 N/m$^2$, preferably at least 0.2, 0.3, 0.4, 0.5, 0.7, 0.9, 1.0, 1.2, 1.5 or 2.0 N/m$^2$, d) in case a stirrer is used for agitation, said suspension is agitated such that the resulting shear rate at the tip of the stirrer is at least 300 s$^{-1}$, preferably at least 500, 700, 900, 1100 or 1300 s$^{-1}$, e) said cells are supplied with at least one gas by exclusive flow, f) said cells are supplied with at least one gas at a flow rate of at most 0.05 l/h, preferably at most 0.02, 0.01 or 0.005 l/h per liter of reactor volume, g) the gas supply has a peak flow rate of 0.05 vvm or less, preferably 0.02, 0.01 or 0.005 vvm or less.

According to a second aspect of the present invention, a method for the recombinant production of a product of interest in human immortalized human blood cells is provided, wherein said cells comprise a gene encoding the product of interest and wherein said cells are cultured according to the method according to the first aspect of the present invention.

Furthermore, the present invention also provides methods and tools that allow the successful scale-up of the fermentation while maintaining the yield and quality of the product.

DETAILED DESCRIPTION OF THE INVENTION

The methods according to the first and second aspect of the invention allow achieving one or more of the following goals: minimised damage to the cells, especially damage induced by gas supply, aeration and/or bubble formation, a high stability and uniformity of the glycosylation structures in case a glycoprotein is expressed, a good production rate, ease of handling, a reduced number of cell clumps, ease of scale up and robustness to process parameter variation.

Unless indicated otherwise the term "methods according to the invention" or "method according to the invention" refers to both the method according to the first and to the method according to the second aspect of the present invention.

The methods according to the invention are in part based on the surprising finding that the cells used according to the present invention show particularly good growth properties (e.g. viability) and a particularly good production of recombinant proteins when the intensity (vigour) of agitation is quite high. This was unexpected because cells usually tend to be damaged by the shear forces induced by vigorous agitation. A surprising finding was that the cells to be used according to the invention have a different sensitivity to shear forces induced by agitation and to shear forces induced by air bubbles. The cells that are used according to the invention are very robust to stirrer induced shear forces (e.g. they tolerate shear forces of e.g. 0.9 N/m$^2$ and shear rates of e.g. 1000 s$^{-1}$), but they are quite sensitive to aeration. Exclusive flow gas supply or gas supply at a low flow rate may also be used to achieve the advantages of the present invention because these measures reduce the shear forces induced by bubbles. It was unexpected that the cells used according to the invention are rather insensitive to shear forces induced by stirring to an extent that allows agitation that is vigorous enough to allow the application of an exclusive flow gas supply. The vigorous agitation has the advantageous effect that a homogeneous mixing and homogeneous growth conditions for all cells are ensured.

In preferred embodiments, the cell suspension is agitated such that the resulting specific power input is at least 0.005 W/kg. The specific power input in particular is the power used for agitation (e.g. for rotating a stirrer or for rotating, rocking, swinging or otherwise agitating the cell culture and/or cell culture vessel) per mass (e.g. kg) or volume (e.g. m³) of the cell culture. Preferably, the specific power input for agitation is at least 0.01, at least 0.015, at least 0.02, at least 0.025, at least 0.03, at least 0.04, at least 0.05, at least 0.075 or at least 0.1 W/kg, more preferred in a range of from 0.015 to 0.03 W/kg, most preferred from 0.018 to 0.025 W/Kg.

The cells to be used according to the invention allow the production of glycoproteins with human glycosylation, which generally leads to improved bioavailability and functionality. This is an important advantage over currently available production systems, which are mainly of rodent origin (e.g. CHO-cells, NSO-cells, Sp2/0 cells). The main advantage of the cell lines is the human glycosylation along with other human posttranslational modifications.

The immortalized human blood cells to be used according to the invention are preferably cells of human myeloid leukemia origin or cells derived therefrom. Preferably the cells are from a cell line, in particular from the K562 cell line (e.g. the K562 cell line available as ATCC CCL 243) or a cell line derived therefrom. Respective cells, cell lines and host cells are described in detail in WO 2008/028686, herein incorporated by reference. However, the methods according to the present invention are also suitable for other suspension cells or cell lines which tolerate high shear stress, in particular for eukaryotic suspension cells or cell lines, preferably human suspension cells or cell lines.

The method for the recombinant production of a product of interest, preferably a glycoprotein, in immortalized human blood cells, preferably cells of myeloid leukaemia origin or cells derived therefrom, allows to produce the product of interest with good yield and homogenous quality even when using different culturing volumes and even when applying high shearing forces induced by stirring. The host cells comprise a gene encoding the product of interest and said cells are cultured according to the method of claim 1. Said gene encoding the product of interest is preferably introduced recombinantly. Said recombinant techniques are well-known and thus, need no detailed description here. E.g. the gene encoding the product of interest can be comprised in an expression vector which is then stably or transiently introduced into the host cells. The product of interest can be of any nature, preferably it is a protein or polypeptide. Preferably, said product is glycosylated. In particular, the recombinant production of pharmaceutically active products such as antibodies or other therapeutically active proteins are of interest. For the large scale production of respective products, fermentation methods are needed, that allow the production of the product of interest with good yield and a good, homogenous quality, even if different culturing volumes are used. Furthermore, the product quality and preferably also the yield should be preferably comparable between different production charges. These advantages can be achieved with the method according to the present invention.

The expressed product of interest is obtained from the cell culture, e.g. by disrupting the cells or by harvesting the secreted product of interest from the cell culture medium. Preferably, the product of interest is purified from the cell culture medium. In this embodiment, the product preferably is secreted by the cells.

Preferably, the cells are cultured by continuous fermentation with cell retention (perfusion), which gives particularly good results. The cells used in the methods according to the invention do not produce recombinant protein in discernible amounts during the stationary phase. Accordingly, perfusion may serve to prolong the exponential (logarithmic) growth phase in which most of the protein is produced. Therefore, using perfusion for cultivation is advantageous when culturing the immortalized human blood cells such as K562 cells or cells derived therefrom.

In perfusion mode, fresh media is preferably continuously supplied. In the same way, cell free supernatant is preferably taken from the bioreactor while cells are preferably held back in the fermenter. An important feature of a perfusion fermenter is the cell retention system. Cells can be held back applying different techniques. For example filtration, centrifugation or sedimentation can be used. In a perfusion method according to the invention, cell retention is preferably achieved by a device selected from the group consisting of a spin filter, a hollow fibre, a continuous centrifuge and an acoustic cell retention system.

Preferably, a continuous centrifuge such as a Centritech Lab continous centrifuge is used for perfusion. Perfusion using the Centritech Lab continuous centrifuge is suitable for perfusion volumes between 0.5 l/d and 120 l/d; for larger cell cultures the Centritech Cell continuous centrifuge may be used. Over this large range of volume the Centritech is using different types of operation. There are several continuous modes: pump mode, valve mode and feed mode and a discontinuous intermittent mode, which is a variation of the pump mode. In discontinuous mode, the centrifuge is operating during the run time which is interrupted by a waiting time. During waiting time the tubing system should be cell free, which is guaranteed by flushing the system after each run using cell free supernatant.

Perfusion is controlled by setting the feed-pump and controlling the harvest pump of the Centritech. According to one embodiment, the rate of perfusion is set between 0.5 V/d (cell culture volumes per day) and 2.5 V/d. In order to adjust the perfusion rate properly to cell requirements, a key parameter (control parameter) is preferably chosen. Ideally, the control parameter is growth/production limiting and easy to measure. Nonetheless, more often the control parameter is not the growth limiting factor. E.g., glucose is set as control parameter.

A perfusion process for the cells used according to the present invention features high cell viability during high density fermentation. During fermentation, there are neither limitations regarding the main substrates e.g. oxygen, glucose, glutamine, nor is any of the proteinogenic amino acid limiting. Additionally, the perfusion process features a constant product quality and especially a constant glycosylation pattern. The fermentation process is preferably controlled at pH 7.2; DOT (dissolved oxygen tension) of 40% and at a temperature of 37° C. Fermentation with said immortalised blood cells can be performed with a high power input (e.g. 0.022 W/m³, as cells tolerate high shear forces in particular in a stirred tank bioreactor.

Under perfusion conditions, the cell concentration usually increases until a limitation is met. This limitation can be either a nutrient or the accumulation of a waste product. Compared to a batch or a fed-batch fermentation much higher cell densities can be reached due to constant media supply and waste product washout. Based upon those higher cell densities superior space-time yields are achieved.

According to one embodiment, cells are removed during cultivation, preferably by bleeding. When bleeding is applied, a certain amount of cells (e.g. 10% of total volume) is taken from the fermenter. Bleeding has the advantage that cells are kept in a growth phase for a longer time at an increased viability, which results in a more stable culture. Several bleeding strategies have been discussed in the literature by Dalm and coworkers, herein incorporated by reference [Dalm et al. 2004], [Dalm et al. 2007].

A particular advantage of the culturing method of the present invention which is important for the recombinant production of a glycosylated product of interest is that said method results in homogenous and highly reproducible glycostructures when expressing e.g. glycoprotein. In a preferred embodiment, the glycosylation structure of a product of interest and/or the production rate of the cells is substantially unaffected by the culture volume. An example is a case wherein cultures (preferably perfusion cultures) in a 1 l reactor and in a 100 l reactor are compared. Preferably, the overall product quality is substantially unaffected by the culture volume. The examples show that the methods according to the present invention are able to achieve these advantages.

According to one embodiment, the cell density in the cell culture reaches at least $1 \times 10^6$/ml. Preferably, the cell density is even higher, e.g. at least 1.5, 2, 3, 4, 5, 6, 7, 8, 9 or $10 \times 10^6$ cells/ml. According to one embodiment, the cell viability in the cell culture is at least 70%, preferably at least 80%, more preferred at least 85%, at least 90% or at least 95%. According to one embodiment, the methods according to the invention the cell density reaches at one point in time at least $5 \times 10^6$/ml at a cell viability of at least 90%. The cell viability in particular denotes the percentage of the number of living cells compared to the number of all cells (living and dead) in a sample.

A preferred achievable peak production rate is at least 25 µg/(mld) (25 µg product per ml cell culture per day), preferably at least 50 µg/(mld), at least 80 µg/(mld), at least 90 µg/(mld) or at least 100 µg/(mld).

In the methods according to the invention preferably a stirrer is used for agitation, in particular an impeller.

The culture of cells is generally contained in a vessel, which may be e.g. a bag for containing a cell culture, preferably a single-use bag, or alternatively a vessel other than a bag, e.g. a tank, container or the like. If a bag is used, it may preferably be combined with a stirrer that is used for agitation. Preferably, a fermenter is used as vessel that is suitable and preferably commonly used for a perfusion method.

In preferred methods according to the invention a device selected from the group consisting of a ring sparger, a micro sparger and a membrane is used for aeration. The methods according to the invention allow using a sparger for gas supply, which would otherwise not be feasible due to the high sensitivity to air bubbles of the cells to be used according to the invention.

According to one embodiment, pulses of at least one gas are given during the culturing process for aeration.

According to one embodiment, the bubble development caused by aeration is limited by the chosen aeration method and wherein the produced bubbles preferably have a size of more than 2 mm, preferably more than 5 mm, more preferably 10 mm or more. As discussed above, bubbles larger than 2 mm and in particular larger than 10 mm result in less shear stress and accordingly, are less lethal to the cells used according to the present invention.

As discussed above, gas supply in general or aeration is preferably achieved by an exclusive gas flow. The term "exclusive flow" in particular refers to supplying gas in a discontinuous manner, as opposed to a constant flow wherein gas is supplied in a continuous manner. The term "aeration" in particular refers to supplying a gas comprising or consisting of oxygen (e.g. air, preferably pure oxygen). Preferably aeration is performed by exclusive flow. A pulse of gas supply (e.g. a gas comprising oxygen, preferably all gases) can according to one embodiment at most be 30 s (or at most 10 s, 3 s or 1 s) in duration. The fraction of time during which the gases are supplied can be at most 25% (or at most 10%, 5%, 2.5% or 1%) of the cultivation (culturing) time over at least 1 h (or at least 2 h or 5 h). Preferably, means for detecting the oxygen saturation in the suspension is used. The gas comprising oxygen is preferably supplied when the detected oxygen saturation is lower than a predefined threshold, such as e.g. a $pO_2$ or DOT of 10%, preferably 2096.25%, 30% or more preferably 35%. Preferably for aeration, pure oxygen is supplied.

Thus, according to one embodiment the oxygen value, respectively the oxygen saturation in the cell culture is determined and wherein oxygen and/or an oxygen containing gas or gas mixture is introduced as a pulse into the cell culture medium if the level of oxygen drops below a predetermined level, e.g. as defined above. This advantageously minimises the aeration and accordingly the bubble formation.

In preferred embodiments, the cells are supplied with at least one gas at a flow rate of at most 0.05 l/h, preferably at most 0.02, 0.01 or 0.005 l/h per liter of reactor volume. In particular, the entire gas supply of the cell culture is 0.05 l/h per liter of reactor volume or less, preferably 0.02, 0.01 or 0.005 l/h per liter of reactor volume or less. The terms "flow rate" and "gas supply" in this respect preferably refer to the mean flow rate or gas supply over the entire culturing process. That means that when using exclusive gas flow, wherein gas is introduced into the cell culture in intermitted intervals, the actual flow rates during the supply intervals may be higher than the above values. However, on average considering the supply intervals and the intervals where no gas is introduced into the cell culture, the overall flow rate or gas supply is preferably at most 0.05 l/h per liter reactor volume, as defined above.

In preferred embodiments wherein gas supply is achieved by exclusive gas flow, the flow rate at any time during the supply intervals (peak flow rate) is 0.05 vvm (volume per reactor volume per minute) or less, preferably 0.02, 0.01 or 0.005 vvm or less.

In certain especially preferred embodiments, in the methods according to the present invention
(i) the specific power input for agitation of the suspension is at least 0.01 W/kg; and
(ii-1) the gas supply with at least one gas or the entire gas supply of the suspension is 0.05 l/h per liter of reactor volume or less, or
(ii-2) the gas supply is achieved by exclusive gas flow and the peak flow rate is 0.05 vvm or less.

Preferably, the specific power input for agitation of the suspension is at least 0.015 W/kg; and the gas supply with at least one gas or the entire gas supply of the suspension is 0.02 l/h per liter of reactor volume or less or, if the gas supply is achieved by exclusive gas flow, the peak flow rate is 0.02 vvm or less. In these embodiments, the shear force resulting from agitation of the suspension is at least 0.1 $N/m^2$, preferably 0.3 $N/m^2$, and/or the shear rate at the tip of the stirrer is at least 300 $s^{-1}$, preferably 500 $s^{-1}$.

According to one embodiment, a base is added during the cultivation to maintain the pH at a predetermined level or pH range. Preferred pH ranges or values are between 5 and 9, more preferably between 6 and 8.5, between 6.5 and 8, or most preferably between 7 and 7.5. The addition of a base is usually required in order neutralize e.g. lactate-formation, or for neutralizing $CO_2$ formation. In the methods known in the prior art, the addition of a base results in cell clumping that is probably induced by the base which can induce cell lysis. Clumping is an aggregation of dead cells. Clumping is in particular a problem in larger scales. The method according to the present invention reduces the clumping formation, probably due to the more vigorous agitation. The methods according to the invention allow reducing the formation of cell clumps. The bases to be added to the cell suspension may be distributed more quickly and evenly. In a preferred method according to the invention the formation of cell clumps is reduced as opposed to a corresponding method comprising none of features a) to f).

Preferably, the base is added in close proximity to the stirrer region. Furthermore, the base is preferably added directly into the cell suspension, i.e. the site of addition is beneath the suspension's surface and the base is not dripped into the suspension.

The cells are preferably cultured in a serum-free medium, e.g. chemically defined GTM media.

In a preferred embodiment of the methods according to the present invention the cell culture medium comprises a shear protective agent, e.g. serum. Poly(ethylene glycol) (PEG), poly(vinyl pyrrolidone) (PVP), poly(vinyl alcohol) (PVA), or Pluronic-F68. The shear protective agent is preferably used at a concentration of <0.01 to 3 g/l. Preferably, the cell culture medium is serum-free.

According to one embodiment, the cell culturing is performed at a pH range between 6.5 and 8, preferably 7 and 7.5; a $pO_2$ of 10% to 90%, preferably 30% to 50%, more preferably 35% to 45% and/or a temperature of 30 to 40° C., preferably 37° C.

According to a preferred embodiment, the glycosylation structure of the product of interest and/or the production rate of the cells is substantially unaffected by the culture volume.

Preferably, the preferred embodiments as disclosed herein as combined with each other. In particular, the following preferred combinations are provided:
feature a) with feature e)
feature a) with feature f)
feature a) with feature g)
feature a) with feature e) and feature g)
feature c) with feature e)
feature c) with feature f)
feature c) with feature g)
feature c) with feature e) and feature g)
feature d) with feature e)
feature d) with feature f)
feature d) with feature g)
feature d) with feature e) and feature g)
feature e) with feature g)
feature a) with feature e) and feature g) and feature c) and/or feature d)

In these combinations, in particular the preferred values and ranges as defined above may be used. In certain embodiments, the above combinations are further combined with one or more of the embodiments defined herein, in particular with feature b).

According to one embodiment, a fermenter is used for cell culturing which has a volume of at least 1 l, preferably at least 10 l, at least 20 l, at least 50 l, at least 100 l, at least 200 l, at least 500 l or at least 1000 l, in particular a volume in the range of 1 l to 1000 l, 1 l to 500 l, 10 l to 250 l or 20 l to 100 l. As discussed above, surprisingly, in particular the product quality but also the productivity is unaffected by the size of the fermenter. This is a particular advantage when altering the scale of the production process. According to one embodiment, the power input is used as scale up criteria and hence the specific power input is kept constant between different fermenter sizes (allowing however, preferably a deviation of approx. 25%, 20%, 15%, 10%, 5%). Preferably, the specific power input is at least 0.005 W/kg, preferably at least 0.01, 0.015, 0.02, 0.025, 0.03, 0.04, 0.05, 0.075 or 0.1 W/kg, more preferred in a range of 0.015 to 0.03, more preferred 0.018 to 0.025 W/Kg.

According to a further aspect the present invention relates to a method for upscaling the culturing or production process used in the methods according to the invention, wherein the power input is used as scale-up criterion. In particular, the power input is kept constant during scale-up, that is the specific power input for the initial, small scale culturing method is in the range of from 75% to 125%, preferably from 80% to 120%, from 85% to 115%, from 90% to 110% or from 95% to 105% of the specific power input for the final, upscaled, large scale culturing method. In particular, the specific power input for the small scale culturing method and/or for the large scale culturing method is at least 0.005 W/kg, preferably at least 0.01, 0.015, 0.02, 0.025, 0.03, 0.04, 0.05, 0.075 or 0.1 W/kg, more preferred in a range of 0.015 to 0.03, most preferred 0.018 to 0.025 W/Kg. The large scale culture preferably has a cell culture volume which is at least 25% larger than the cell culture volume of the small scale culture. More preferably, the cell culture volume of the large scale culture is at least 50% larger, at least 100% larger, at least 1.5-times larger, at least 2-times, at least 5-times, at least 10-times, at least 20-times, at least 50-times or at least 100-times larger than the cell culture volume of the small scale culture.

In particular, the present invention relates to a method for altering the scale of the recombinant production of a protein of interest, comprising the following steps:
providing a first vessel for culturing cells,
providing immortalised human blood cells or cells derived therefrom,
providing a first suspension of said cells,
introducing the first suspension to the first vessel,
performing the culturing or production method according to the present invention, in particular the method according to any of claims 1 to 25,
optionally noting the glycosylation structure of a glycoprotein of interest produced in the first suspension and/or the production rate of the cells of the first suspension,
providing a second vessel for culturing cells, which has an internal volume different from the first vessel,
providing a second suspension of said cells,
introducing the second suspension to the second vessel,
performing the culturing or production method according to the present invention, in particular the method according to any of claims 1 to 25,
optionally noting the glycosylation structure of the glycoprotein of interest produced in the second suspension and/or the production rate of the cells of the second suspension,
optionally comparing the glycosylation structure of the glycoprotein of interest produced in both suspensions and/or the production rate of the cells of both suspensions.

The term "altering the scale" preferably refers to upscaling, i.e. increasing the culture volume.

The methods according to the invention (e.g. high agitation and low aeration) allow good growth of the cells to be used according to the invention. It was found that they may be cultured in stirred tank bioreactors and a number of other vessels, herein collectively also referred to as fermenter (e.g. T-flasks, spinner and wave bioreactor) which are inhomogeneous in volume and geometry. For the stirred tank, a viable cell density of about $2*10^6$ cells/ml along with a high viability >95% can be achieved. In perfusion mode, cells grow to high cell densities of up to $10^7$ cells/ml along with a high viability of >90%. An good specific productivity may e.g. be obtained by perfusion.

Standard conditions are pH 7.2; dissolved oxygen tension (DOT) 40% and temperature 37° C., although the method according to the invention is robust with regard to process parameter variation. Using low gas flow and a ring sparger gives surprisingly good results.

The product quality obtained by the method according to the invention is very high, so the choice for the production method can be made based on productivity and economic considerations. When expressing an antibody using the methods according to the present invention it was found that the glycosylation pattern was comparable and thus unaltered when using a 1 l scale compared to 10 l and 100 l bioreactors of different geometric proportions. Based upon high shear stress robustness of the cells that are used according to the invention (at least a 10-fold increase compared to CHO cells), the scale up may be performed at a constant specific power input. Qualitative and quantitative performance evaluation of the 1 l, 10 l and 100 l bioreactors and a panel of biochemical characterization tests show that the comparability of the process (method) and the product was well maintained during the process of scale up.

CITED LITERATURE

Figure 1:
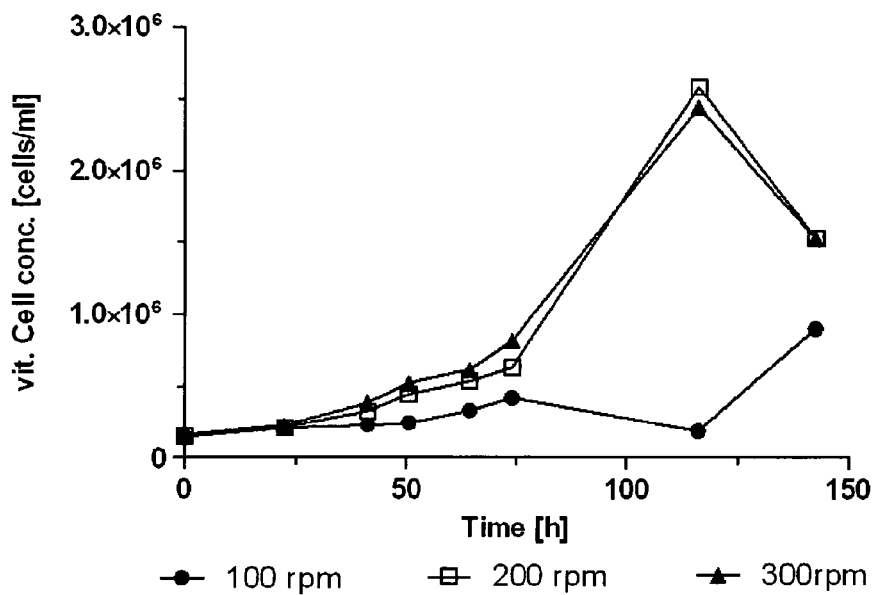
FIG. 1 shows the results of a set of experiments for GlycoExpress A hPM (PankoMab, an anti-MUC1 antibody) comparing different power input for 100 rpm (0.0007 W/kg), 200 rpm (0.006 W/kg) and 300 rpm (0.02 W/kg). Data is shown for viable cell concentration (A), productivity (B) and vitality (C).
Figure 1:
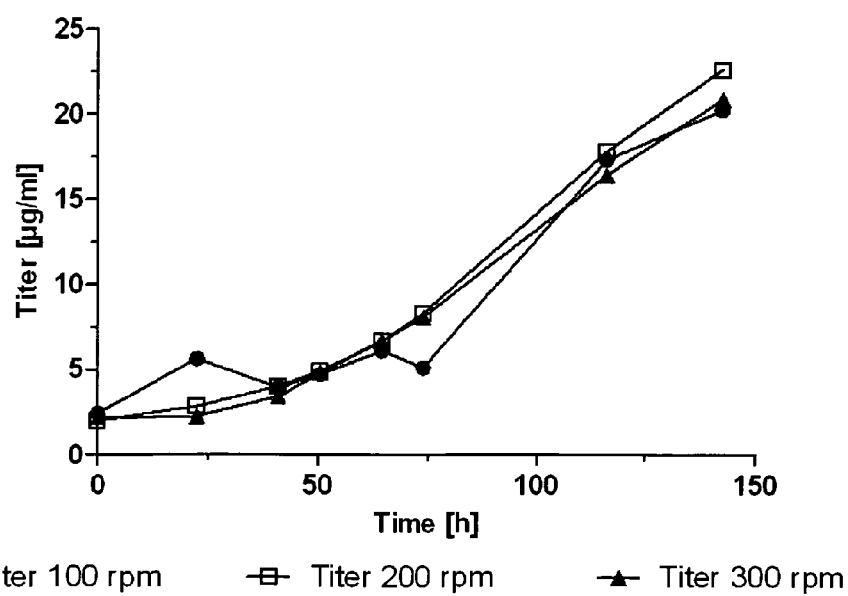

[Ahn et al. 2008] Ahn, Woo Suk, J.-J. Jeon, Y.-R. Jeong, S. J. Lee and S. K. Yoon (2008). Effect of culture temperature on erythropoietin production and glycosylation in a perfusion culture of recombinant CHO cells. Biotechnol Bioeng, 101(6):1234-1244.

[Godoy-Silva et al. 2009] Godoy-Silva, Ruben, J. J. Chalmers, S. A. Casnocha, L. A. Bass, and N. Ma (2009). Physiological responses of CHO cells to repetitive hydrodynamic stress. Biotechnol Bioeng, 103(6):1103-1117.

[Kunkel et al. 1998] Kunkel, J. P., D. C. Jan, J. C. Jamieson, and M. Butler (1998). Dissolved oxygen concentration in serum-free continuous culture affects N-linked glycosylation of a monoclonal antibody. J Biotechnol, 62(1):55-71.

[Lipscomb et al. 2005] Lipscomb, Matthew L. L. A. Palomares, V. Hernandez, 0. T. Ramirez, and D. S. Kompala (2005). Effect of production method and gene amplification on the glycosylation pattern of a secreted reporter protein in CHO cells. Biotechnol Prog, 21(1):40-49.

[Motobu et al. 1998] Motobu, Maki, P.-C. Wang, and M. Matsumura (1998). Effect of shear stress on recombinant chinese hamster ovary cells. Journal of Fermentation and Bioengineering, 2:190-195.

[Muthing et al. 2003] Muthing, Johannes, S. E. Kemminer, H. S. Conradt, D. Sagi, M. Nimtz, U. Karst, and J. Peter-Katalinic (2003). Effects of buffering conditions and culture pH on production rates and glycosylation of clinical phase I anti-melanoma mouse IgG3 monoclonal antibody r24. Biotechnol Bioeng, 83(3):321-334.

[Senger and Karim 2003] Senger, Ryan S and M. N. Karim (2003). Effect of shear stress on intrinsic CHO culture state and glycosylation of recombinant tissue-type plasminogen activator protein. Biotechnol Prog, 19(4):1199-1209.

[Tachibana et al. 1994] Tachibana, H., K. Taniguchi, Y. Ushio, K. Teruya, K. Osada, and H. Murakami (1994). Changes of monosaccharide availability of human hybridoma lead to alteration of biological properties of human monoclonal antibody. Cytotechnology, 16(3):151-157.

EXAMPLES

Example 1

Preculture

Precultures are grown in cell culture flasks (TPP/Biochrom, Germany). Flasks are used up to 5 ml (T25, 25 cm$^2$ area), 30 ml (T75, 75 cm$^2$) and 75 ml (T150, 150 cm$^2$) of suspension volume. Cells are maintained in the logarithmic growth phase by splitting every 2-3 days and setting cell concentration to 0.15*10$^6$ cells/ml after splitting. Addition of Methotrexate (Sigma-Aldrich, Germany) and Puromycin (Takara Bio Europe, France) is done in a clone dependent way on a weekly basis or permanently at different concentration. Cells are cultivated in incubators (Integra Biosciences IBS, Biosafe plus, Switzerland or Thermo/Heraeus BBD 6220, Germany) at 37° C., 8% carbon dioxide and 95% rel. humidity.

Example 2

Spinner Culture

Starting with volumes of 125 ml of cell suspension, a spinner preculture is carried out using spinner flasks (Integra Biosciences IBS, Cellspin, Switzerland). Three different volumes (0.25 l, 0.5 l, 1 l) of spinner flasks are used. The spinner speed is set to 60 rpm while operating the system inside an incubator (Integra Biosciences IBS, Biosafe plus, Switzerland) at 3° C., 8% carbon dioxide and 95% rel. humidity. Spinner flasks are inoculated with 0.15*10$^6$-0.3*10$^6$ cells/ml. For preculture purposes, cells are maintained in logarithmic growth phase by increasing suspension volume every 2-3 days and setting cell concentration 0.15*10$^6$ cells/ml after splitting.

Prior to establishing a fermentation process for GlycoExpress A and GlycoExpress B cells (which are cells of a cell line derived from K562), growth is analyzed in spinner cultures. Besides T-flasks, spinners and shake flasks are used for preculture purposes. Compared to T-flasks, both spinners and shakers have improved mass transfer properties resulting in increased $k_L a$-values.

Growth profiles have been analyzed in parallel for GlycoExpress A hPM cells in batch experiments. Cells grow comparably in all three different systems. Cell concentration in T-flasks is slightly lower compared to spinner and shaker cultures.

Although reaching lower cell densities, cell culture in T-flasks shows the highest lactate concentration. Concluding, spinner bottles and shake flasks are equally well-suited for cultivating cells. Both seem to provide slightly better growth compared to T-flasks and therefore are well suited for preculture prior to fermentation. This also hints to a robustness of the cell line concerning cultivation.

Example 3

Fermentation Biostat B-DCU 2 l

Laboratory scale fermentations are carried out using a Sartorius Biostat B-DCU 2 l system (Sartorius, Germany). Double wall Univessel 2 l (Sartorius, Germany) fermentation vessels have a working volume of min. 0.8 and max. 2 liters. Generally, fermentations are performed at 1 liter working volume. All fermenters are sterilized in a Systec V-150 autoclave (Systec, Germany). Gas mixing supports four different gases: nitrogen, oxygen, carbon dioxide and compressed air. Oxygen, carbon dioxide and compressed air are operated by mass flow controllers, while nitrogen is controlled using a variable area flow-meter Q-Flow (Vögtlin Instruments, Germany). Aeration can also be controlled by setting a total flow for all gases. Gas supply and exhaust gas are filtered using Sartorius Midisart 2000 0.2 µm PTFE filters (Sartorius, Germany). The dissolved oxygen concentration is measured online using Mettler Torledo InPro 6800 electrodes (Mettler-Torledo, Switzerland). Addition of base (0.5 M NaOH) and addition of carbon dioxide are used to control the pH value. The pH-value is measured online using a Mettler-Torledo 405-DPAS-SC-K8S electrode (Mettler-Torledo. Switzerland). Base is added via a Watson Marlow 100 OEM pump (Watson Marlow, England). Two additional Watson Marlow 100 OEM pumps (Watson Marlow, England) and one Watson Marlow 313 OEM pump (Watson Marlow, England) are used for cell harvest, inoculation or other purposes. Feed-medium is added via a Watson Marlow 101U/R (Watson Marlow, England) using a Sartorius LE1000 l balance (Sartorius. Germany) and a gravimetric flow controller. Reactor weight was measured using an Economy Series EA60EDE-1 balance (Sartorius, Germany). Cells are agitated with one or two 3-blade segment impellers 1-2 l, adjust, compl., ø54/10 H7 (Sartorius, Germany). The agitator shaft is powered by a Kollmorgen Seidel 65M 27LL-4.500 motor (Kollmorgen Seidel, Germany). Depending of the reactor volume one or two stirrers are applied: e.g. for the Biostat B-DCU 2 l one stirrer is used when working with 1 l working volume, while two stirrers are used for a 2 l fermentation. Process cooling is implemented using an autonomous loop and a Frigomix 1000 refrigeration machine. (Sartorius, Germany)

Batch Fermentation

Most fermentations in this work are performed using the Sartorius Biostat B-DCU system with a working volume between 0.8-2 liters (preferred volume is 1 l). Fermentation is started with a cell density of $0.15*10^6$-$0.3*10^6$ cells/ml at 37° C., pH 7.2 and an air saturation of 40% DOT unless otherwise noted. Carbon dioxide gas flow/0.5 NaOH is used to regulate the pH. DOT is kept at 40% by using compressed air or pure oxygen. Both pH and DOT are PID-controlled. Prior to optimization of power input, different aeration systems are tested. These fermentations are performed at 50 rpm stirrer speed, 37° C., 40% DOT, pH 7.2 at 1.5 l working volume. Ring sparger, micro sparger and membrane aeration (Sartorius, Germany) are tested in parallel runs.

Continuous Fermentation

Continuous fermentation is carried out using four different techniques for cell retention. All fermentations are performed using the Sartorius Biostat B-DCU system with a working volume between 1-1.5 liters.

1. Continuous Centrifuge: Centritech Lab II or Centritech Lab III (Berry Wehrmiller, Carr Centritech, USA)
2. Internal Spinfilter: Sartorius Spinfilter 2 l 20 µm (Sartorius. Germany)
3. External Hollow Fibre: Amersham Biosciences CFP-4E5A, 0.45 µm, 1200 $cm^2$ (Amersham Biosciences, USA)
4. Acoustic Cell Retention: Biosep APS 990 (Applisens/Applikon biosciences, Netherlands)

In the later stages of process development, all continuous fermentations have been carried out using the Centritech Lab II or Centritech Lab III (Berry Wehrmiller, Carr Centritech, USA) continuous centrifuge. The Centritech provides different modes of operation for different sizes of reactor volume. Centrifugation is performed using the "Intermittent Pump Mode" for lab scale fermentations at 1 l working volume. Fermentation in 10 l or 100 l scale uses the "Pump mode" or "Feed mode" in continuous operation. Perfusion is controlled via two balances. The feed uses a gravimetric flow controller, while harvest is set via changing the Centritech control parameters. The Centritech Lab II and Lab III centrifuges are not directly connected to the OCU. Perfusion in 100 l scale is controlled via a level sensor controlling the feed while the Centritech harvests continuously.

Example 4

DASGIP Bioreactor System

Additional laboratory scale fermentations are carried out using a DASGIP Bioreactor System (DASGIP, Jülich, Germany). Consisting of different modules the DASGIP Bioreactor System can operate four bioreactors at the some time controlling pH (module PH4/PO4), DOT (module PH4/PO4), temperature (module TC4/SC4), agitation (module TC4/SC4) and liquid feeds (module MP8) independently for each reactor. Fermentation vessels (DASGIP. Germany) have a working volume of 0.6-1 l. Temperature control is guaranteed using heating sleeves. DASGIP systems are equipped with peristaltic pumps featuring variable speed drives. The flow rate of every pump can be user programmed in order to be controlled by a separate function based on online data. Concurrent feedback control of multiple analyses for both nutrients and metabolites can be achieved. Gas supply is controlled using the MX4/4 module. Gas mixing supports four different gases: nitrogen, oxygen, carbon dioxide and compressed air which are operated by mass flow controllers. Gas supply and exhaust gas is filtered using Sartorius Midisart 2000 0.2 µm PTFE filters (Sartorius, Germany). Addition of base (0.5 M NaOH) and addition of carbon dioxide are used to control the pH value. pH is measured online using a Mettler-Torledo 405-DPAS-SC-K8S electrode (Mettler-Torledo, Switzerland). All fermenters are sterilized in a Systec V-150 autoclave (Systec, Germany). Cells are agitated with one 3-blade segment impeller (DASGIP, Jülich Germany). The agitator shaft is powered by a magnetic stirrer.

Example 5

Fermentation 10 l Laboratory Scale

Laboratory scale fermentations are carried out using a Sartorius Biostat C-DCU3 10 l system (Sartorius, Germany). A stainless steel fermentation vessel is used with a working volume of minimal 4 and maximal 10 liters. Generally, batch fermentations are performed at 10 l working volume, while perfusion is carried out at 5 l working volume. The 10 l CDCU is similarly configured as the 2 l B-DCU bioreactors. Gas mixing supports four different gases: nitrogen, oxygen, carbon dioxide and compressed air. Oxygen, carbon dioxide and compressed air are operated by mass flow controllers, while nitrogen is controlled using a variable area flow-meter Q-Flow (Vögtlin Instruments, Germany). Aeration can also be controlled by setting a total flow for all gases. Gas supply and exhaust gas are filtered using Sartorius Mini or Sartorius Junior 0.2 μm PTFE filters (Sartorius, Germany). Dissolved oxygen concentration is measured online using Mettler Torledo InPro 6100/120/T/N electrodes (Mettler-Torledo, Switzerland). Addition of base (0.5 M NaOH) and addition of carbon dioxide are used to control the pH value. The pH value is measured online using a Mettler-Torledo 405-DPAS-SC-K88 electrode (Mettler-Torledo, Switzerland). Base is added via a Watson Marlow 100 OEM pump (Watson Marlow, England). Two additional Watson Marlow 100 OEM pumps (Watson Marlow, England) are used for cell harvest, inoculation or other purposes. Feed-media is added via a Watson Marlow SCI323 (Watson Marlow, England) using a Sartorius EA150CE balance (Sartorius. Germany) and a gravimetric flow controller. Cells are agitated with one or two 3-blade segment impellers 5-10 l, adjust, compl., ø54/10 H7 (Sartorius, Germany). The agitator shaft is powered by a Kollmorgen Seidel 65M 57SL-3000 motor (Kollmorgen Seidel, Germany). Depending of the reactor volume one or two stirrers is/are applied: e.g. for 10 l C-DCU: one stirrer for 5 l, two stirrers for 10 l. Process cooling is implemented using an autonomous loop with either a Frigomix 1000 refrigeration machine (Sartorius, Germany) or tab water cooling.

Example 6

Fermentation 100 l Production Scale

Production scale fermentation is carried out under clean room conditions. Production runs use an Applikon 100 l (Applikon, Belgium) fermenter for cell culture. Software BioXpertXP is used for process monitoring and data logging. Similar to lab scale fermentation, gas mixing supports four different gases: nitrogen, oxygen, carbon dioxide and compressed air which are operated by mass flow controllers. pH and DOT are controlled using Mettler-Torledo electrodes (Mettler-Torledo. Switzerland) for measurement.

Example 7

Fermentation—Single Use

Additional lab scale fermentations are operated with a Wave bioreactor. Temperature, rocking speed and rocking angle are measured and controlled using a Wave Cellbase 20 SPS platform (Wave Biotech AG, Switzerland). DOT, pH and aeration are controlled by a Wavepod-R (GE Healthcare, USA) version. Set points are temperature 37° C., pH 7.2 rocking speed: 12 rpm and angle 9°. The initial cell concentration is set to $1.5*10^5$ cells/ml. Perfusion was operated using Centritech Lab II and Lab III respectively (BerryWehrmiller, Carr Centritech, USA). The wave cell culture bag was designed using a dip tube. Tubes are connected using either Luer-Lock or MPC-adapters. All connecting is performed beneath a laminar flow (Thermo Scientific, USA).

Example 8

ELISA

Antibody concentration is generally determined using enzyme linked immunosorbent assay (ELISA). A volume of 50 μl anti-human anti Ig-kappa antibody (BD Biosciences, USA) is used as a coating antibody at 1 μg/ml in PBS for at least 12 h at 4° C. Non specific binding sites are blocked for 30 min with 2% bovine serum albumin (BSA) (Roth, Germany) in PBS. Samples are diluted in 1% BSA/PBS and 50 μl are incubated for 1 hour. Quantification of data is reached by using Erbitux as standard. Erbitux is used in 10 μg/ml, 8 μg/ml, 6 μg/ml, 4 μg/ml, 2 μg/ml, 1 μg/ml, 0.75 μg/ml, 0.5 μg/ml and 0.25 μg/ml. 50 μl of rabbit anti-human IgG (H+L) POD (Jackson ImmunoResearch, United kingdom) are used as a secondary antibody. Incubation is for 1 hour. Finally, 100 μl Tetramethylbenzidin (TMB) One Component HRP Microwell Substrate (Tebu-Bio Laboratories, Germany) are applied for detection. Reaction is stopped with 50 μl $2.5NH_2SO_4$ (Sigma, Germany) and measured at 450/630 nm wavelength.

Antigen-Binding ELISA

Antigen binding of human PankoMab is measured by binding to glycosylated and nonglycosylated MUC1-peptides in an antigen ELISA. Glycosylated MUC1 peptides are coated at equal molarities in PBS for at least 12 h at 4° C. Non specific binding sites are blocked for 30 min with 2% bovine serum albumin (BSA) (Roth, Germany) in PBS. Samples of human PankoMab are diluted in 1% BSA/PBS to concentrations of 0.4 μg/ml and 0.8 μg/ml and 50 μl are incubated for 1 hour. Calibration is performed using a cell culture supernatant standard (dilution: 1:100; 1:200; 1:400). 50 μl of rabbit anti-human IgG (H+L) POD (Jackson ImmunoResearch, United kingdom) are used as a secondary antibody. Incubation is for 1 hour. Finally, 100 μl Tetramethylbenzidin (TMB) One Component HRP Microwell Substrate (Tebu-Bio Laboratories, Germany) are applied for detection. Reaction is stopped with 50 μl 2.5N $H_2SO_4$ (Sigma, Germany) and measured at 450/630 nm wavelength. The Antigen-ELISA is analyzed using a regression for the supernatant standard. Specification for high product quality is binding to glycosylated peptide with an optical density (OD) higher than 0.3. Additionally, binding ratio of non-glycosylated MUC1 peptide to glycosylated MUC1 has to be <5% in order to comply with the specification.

Example 9

Size Exclusion Chromatography

The percentage of monomeric antibody is determined by using size exclusion chromatography (SEC). Chromatography is run using a Superdex 200 10/300 GC (GE Healthcare, USA) column on an Akta prime (GE Healthcare, USA) system. Samples are diluted with PBS to a sample size of 250 μl containing approx. 50-200 μg of protein. Samples are injected in a bubble-free way using a 200 μl sample loop. The running buffer for analysis is PBS, the flow rate is set to 0.5 ml/min. After elution the chromatogram peak area is analyzed with regard to monomer, dimer and multimer content.

Example 10

Glycan Analysis

Monosaccharide Analysis

For glycan monosaccharide analysis the glycosylated antibody is hydrolyzed with trifluoracetic acid resulting in a release of monosaccharide moieties from the glycan chain. Additionally, N-acetylglucosamine and N-acetylgalactosamine are deacetylated to glucosamine and galactosamine through the action of trifluoracetic acid. The mixture of monosaccharides is separated and quantified by means of high performance liquid anion exchange chromatography with pulsed amperometric detection (HPAEC-PAD).

Glycoprofiling

For glycoprofiling the intact N-glycans are released from the protein core in gel digestion with PNGase. N-glycans are washed out of the gel and subsequently labelled with the fluorescence marker 2-aminobenzamide. The purified sample of labelled N-glycans is separated by means of normal phase chromatography (NP-HPLC) or hydrophilic interaction chromatography (HILIC) with fluorometric detection. NP-HPLC allows for the separation of most N-glycans. HILIC-HPLC allows the separation of N-glycan structures containing bisecting N-acetylglucosamine in contrast to NP-HPLC. Peaks are assigned to glycan structures by comparison of retention times with a database. Additionally, structures are confirmed by MALDI-TOF mass spectrometry and arrays of enzymatic digestions employing exoglycosidases.

Separate Analysis of Fc/Fab Glycosylation

Whereas Fc glycosylation has an impact on the effector function of antibodies. Fab glycosylation influences the interactions of the antibody with an antigen. Therefore, a basic interest of glycan analysis is to determine whether both parts. Fc and Fab are glycosylated, and secondly which differences are observed between the glycosylation patterns of both sites. The complete cleavage of an antibody with papain results in the generation of one Fc fragment and two Fab fragments. Separation of the fragments is performed employing affinity chromatography on protein A solid phase. Protein A binds specifically the Fc fragment as well as the undigested antibody. Fc fragment and undigested antibody bind to Protein A while Fab can be found in the flowthrough. An elution step with 0.1 M citrate, 0.15 M sodium chloride at pH 2.2 allows for release of the Fc fragment whereas undigested antibody. After separation of Fc from Fab part the N-glycans of each fragment are applied for glycoprofiling. Based on the finding the spectra the corresponding structures are classified for the following features: presence or absence of fucose, presence or absence of bisecting GlcNAc, distribution of galactosylation states, distribution of sialylation level (N0, A1, A2) and antennarity.

Example 11

Product Characterization Spinner Culture

The spinner culture supernatant of GlycoExpress A hPM (human PankoMab) is purified using a Protein A-column. After elution, the purified antibody is characterized. The purified antibody shows a specific binding to the bioactivity antigen ELISA which complies with the specification, clear bands in SDS-PAGE indicating high purity and also is of highly monomeric antibody structures (97%). Concerning glycan profile, the product shows diantennary structures along with high values of sialylation and galactosylation. Glycan profile is analyzed from stationary phase antibody.

In order to analyze product quality during the different growth phases, three different harvests are performed representing the three different growth phases. First harvest (exponential phase) is collected after approximately 48 h of culture. Cells are in exponential growth ($\mu>0$). Second harvest is gathered after approximately 140 h of culture in stationary phase. At this point, cells do not grow significantly ($\mu=0$), but viability is high (approx. 95%). Third harvest is collected during death after approximately 210 h. Viability drops significantly (approx. 80%) and living cell concentration declines ($\mu<0$). Antibody is harvested, purified using Protein A and analyzed for different stages of growth. The results indicate clear bands for heavy- and light antibody chain. There is no visible product degradation during the different stages of growth. Concluding, spinner cultures provide a highly monomeric product (determined by size exclusion chromatography (SEC)) which binds specifically in the antigen ELISA and shows no impurities in SDS-PAGE. Glycan profile is also analyzed for stationary growth phase. During further process development, a main goal is to maintain this high product quality.

Example 12

Batch Fermentation

It was found that the growth of the GlycoExpress cell lines is very robust concerning process conditions and highly unaffected by shear forces which are induced by stirring. In contrast, cells are very sensitive to aeration with regard to bubble size and gas flow rate:

12.1 Aeration

Aeration is critical to a biotechnological process, as oxygen supply is essential for animal cells. Yet, bubbles can create intensive shear forces. During cultivation in T-flasks or spinner bottles, no aeration is applied. In fermenters, which generally have much larger volumes, oxygen or air has to be supplied in order to prevent oxygen limitation. Additionally, pH control generally works with addition of carbon dioxide, which needs to be supplied. Therefore, three different kinds of gas supply are tested in the bioreactor. Parallel batch fermentations using GlycoExpress A hPM are carried out in order to minimize variations based upon e.g. different precultures. Fermentations are performed using a ring sparger, a micro sparger and membrane aeration. A ring sparger supplies the bioreactor with rather large bubbles. In contrast to this, a micro sparger creates much smaller bubbles by using a porous gas permeable structure. Ring spargers and micro spargers supply cells using convection, which is influenced by the power input into the bioreactor. At higher power input there is a much better mass transfer, which can reduce the gas flow rate required to maintain a dissolved oxygen tension (DOT) setpoint. Finally, membrane aeration does not create bubbles at all, supplying cells based upon diffusion only. Therefore, membrane aeration is the most cautions method of supplying cells with gas. When membrane aeration is applied there is no bubble based shear stress.

All three different types of aeration are tested for a clone of GlycoExpress A hPM. The parallel fermentations are analyzed with regard to viable cell concentration, productivity and viability. Results show similar growth to a maximal cell density of $2*10^6$ cells/ml and antibody concentration of approx. 20-25 µg/ml for both micro sparger and membrane aeration. Membrane aeration results in a very high vitality of=95%, while micro sparger aeration leads to ca. 90% vitality. Thus, using the ring sparger cells grow to a maximal cell density of $0.7*10^6$ cells/ml and a product concentration of 10 µg/ml. While ring sparger and micro sparger viability drops in the mid and late stages of the fermentation, membrane aeration ensures a very high viability during the process. This indicates bubble induce cell damage when working with ring or microsparger. Highest damage is caused by ring sparger bubbles as viability drops from 92% to 74%. Micro sparger viability is reduce to 84% while membrane aeration keeps an very high viability of 95% during the whole process.

The ring sparger is chosen for further development. This is based on technical and GMP-related limitations in large vessel fermentations. Firstly, membrane aeration is highly costintensive due to high membrane area in production scale, e.g. membrane tubes have to be replaced after every fermentation due to GMP-principles. Secondly, required membrane area increases even more in production scale which may lead to mixing problems due to flow obstruction. Concerning micro spargers it is supposed that they lead to heavy foaming problems in production scale, which could result in the need of antifoam reagents being hard to degrade in downstream processing. Consequently, working with a ring sparger, an increase power input will result in a reduced gas flow rate as mass transfer increases (e.g. Sherwood number increases with increasing Reynolds number).

12.2 Constant Flow Vs. Exclusive Flow

There are two different modes of aeration in a fermenter. The first is to apply a constant flow rate and mix four gases (air, oxygen, nitrogen and carbon dioxide) based upon the cells requirements. The second is not to mix a constant gas flow, but to exclusively give a pulse of required gas. The exclusive flow system gives much better growth and viability. At constant flow rates, cells are damaged more with increasing flow. A net of batch fermentations, performed at flow rates of 0.01 l/h, 0.05 l/h and 0.1 l/h, showed loss of viability at flow rates above 0.01 l/h per liter of reactor volume. Consequently, the exclusive flow system is chosen in order to control fermentation of GlycoExpress cells in a bioreactor. Additionally, fermentation in the wave bioreactor system showed promising results. Using this type of aeration, GlycoExpress cells grow very well.

Summing up, aeration is a very critical parameter. Cell damage due to aeration has been observed on various occasions. The aeration rate has to be set as low as possible in order to reduce the damage. In the following all fermentations are run with an exclusive flow gas-mixing instead of a constant flow gas-mixing. Limiting bubble based aeration is crucial during all steps of development. Therefore, fermentations are preferably performed using pure oxygen supply instead of compressed air.

12.3 Power Input

After setting the type of aeration, next step in optimization was to test different power inputs. Due to possible shear damage in the fermenter, first fermentations are performed at a very low stirrer speed of 50 rpm (this equals a tip speed of 0.14 m/s and a power input of $9*10^{-5}$ W/kg, see table 2 below. Aeration related experiments are conducted using a stirrer speed of 100 rpm leading to a low power input. In order to remain homogeneity especially at high cell densities but also at higher fermenter scales, a higher power input is preferred. The higher power input is also supposed to reduce the gas flow rate needed for aeration, which should result in less bubble based damage.

Power input is tested in batch mode using different stirrer speeds. In a primary set of experiments 100 rpm, 200 rpm and 300 rpm are tested. Table 1 shows agitation characteristics (power input, tip speed, shear tip rate and Reynolds number) for different stirrer speeds between 50-400 rpm.

TABLE 1

Agitation characteristics in 2 l Sartorius B-DCU bioreactor for different agitation speed. Data is based upon 1 l culture volume and the utilization of one 3-blade segment impeller for agitation.

| Agitation [rpm] | Power Input [W/kg] | Tip Speed [m/s] | Shear Rate at Tip [1/s] | Reynolds |
|---|---|---|---|---|
| 50 | 0.0001 | 0.14 | 200 | 3700 |
| 100 | 0.0007 | 0.28 | 284 | 7400 |
| 200 | 0.006 | 0.58 | 400 | 14800 |
| 300 | 0.020 | 0.85 | 492 | 22100 |
| 400 | 0.048 | 1.13 | 568 | 29500 |

The results are depicted in FIG. 1. While 200 rpm and 300 rpm show similar cell density up to $2.5*10^6$ cells/ml, cells do not grow higher than $1*10^6$ cells/ml when stirrer speed is set to 100 rpm. Titer concentration reaches similar levels in all three fermentations of about 25 µg/ml. Despite increasing shear forces, vitality is highest at 200 rpm and 300 rpm. When using 100 rpm, vitality drops to below 80%. Later on, when working on scale up for 100 l scale, mixing became an urgent concern again. Fermentations using 200 rpm and 400 rpm of stirrer speed show comparable results. Working with 400 rpm, cells appear to grow slightly faster, but do not reach as high vital cell concentrations and productivity. Nonetheless, 400 rpm seem to be suited for fermentation, because 400 rpm results in a very high viability (>90%) during logarithmic growth indicating no shear induced damage. Summarizing, stirrer speeds between 200 rpm and 400 rpm show comparable growth. Bubbles influence the viability in a much more negative way than the stirrer induced shear forces. A stirrer speed of 300 rpm (power input: 0.02 W/kg) is set as standard agitation rate for fermentation in 2 l laboratory scale.

12.4 Robustness to Process Parameters

Batch fermentations are performed applying a ring sparger and a power input of 0.022 W/hkg. A total of 16 runs using GlycoExpress A hPM is analyzed. Process values have been set the following way: pH (7.0; 7.2; 7.4), DOT (20%; 40%; 60%) and temperature (36° C., 3° C., 38° C.). There was no influence with regard to growth and productivity in changing the process parameters pH. DOT and temperature in the tested range during a batch fermentation. This means that there is no correlation for changing process parameter with regard to the responses. There was no correlation either between the initial cell number (varying between about $1.2-1.8*10^5$ cell/ml) and the final batch productivity or maximal cell density. As a consequence, also the process of inoculation can consequently be regarded as robust.

Unless noted otherwise, all fermentations are carried out under standard conditions of pH 7.2, DOT 40% air saturation and a temperature of 3° C. These conditions are also applied to perfusion processes.

12.5 Growth-Dependent Production

It was found that as cells grow in batch fermentation, productivity and growth are closely linked to each other as cells do not produce during stationary growth phase. Batch cultures of GlycoExpress A hPM were analyzed regarding their growth and productivity. Antibody production was strongly dependent on cell growth. During stationary phase in fermentation, antibody concentration did not increase.

Statistical testing was applied using cell concentration as influence variable and productivity as response variable. Using a linear regression between cell concentration and productivity, a strong correlation is found ($R^2=0.994$). Consequently, production is linked to growth and cells do not produce any antibody during stationary phase. This gives a major difference to other production systems, like CHO-cells, where most of the product is produced during stationary growth phase. This result is very important for process development. It gives rise to a preferred use of a perfusion process instead of a fed-batch process as most fed-batch work with an extended stationary phase for product accumulation. As another consequence, cell growth should be a major aim for both perfusion and fed-batch process development.

For further analysis of growth dependent productivity, quantitative m-RNA levels were analyzed using reverse transcription polymerase chain reaction (RT-PCR) in logarithmic and stationary growth phase. The results showed a constant level of housekeeping gene expression (actin and GAPDH) in both logarithmic and stationary phase along with constant levels of mRNA for the recombinantly expressed protein ($V_H$ and $V_L$). These results give evidence that both are equally expressed in logarithmic and stationary growth phase. It can be concluded that the reason for declining productivity in stationary phase is likely to be post-transcriptional.

12.6 Confirmation of Product Quality for Batch Fermentation

Batch fermentations were performed under standard conditions (pH 7.2, DOT 40%, 37° C.) in order to analyze product quality and to compare the results with the quality of the spinner product. Generally, the product quality of GlycoExpress A hPM is little different from spinner-produced product (spinner product is shown Table 1). There is an almost unaffected number of multimers with a decreased amount of about 2% antibody multimers in batch culture (compared to 3% in the spinner culture product). Additionally, bioactivity ELISA shows high, specific binding in both spinner and batch fermentation and SDS-PAGE is also unaffected. The glycosylation profile is comparable to the glycan profile of a spinner culture.

12.7 Conclusion Batch Fermentation

The human cells of myloid leukemia origin can be cultured in batch fermentation. Compared to spinner culture, the batch fermentation results in slightly improved cell densities along with slightly higher productivity (about 10% increase, data not shown). The fermentation process can be performed at high agitation as cells are not sensitive to stirrer induced shear forces. Additionally, the process shows a high robustness towards fermentation process conditions giving good growth and productivity for a broad range of pH. DOT and temperature set points. However, cells are sensitive to aeration, hence bubbles should be avoided by using exclusive flow aeration. Therefore applying a high power input is useful as mass transfer increases. In order to increase productivity, perfusion fermentations are performed as described below. For perfusion processes, the process conditions are taken over from the batch culture.

Example 13

Perfusion

It was found that continuous fermentation with cell retention (perfusion) enables fermentation of the human cells of myloid leukemia origin at high cell density along with good specific productivity and highly stable glycosylation.

13.1 Results

Figure 2:
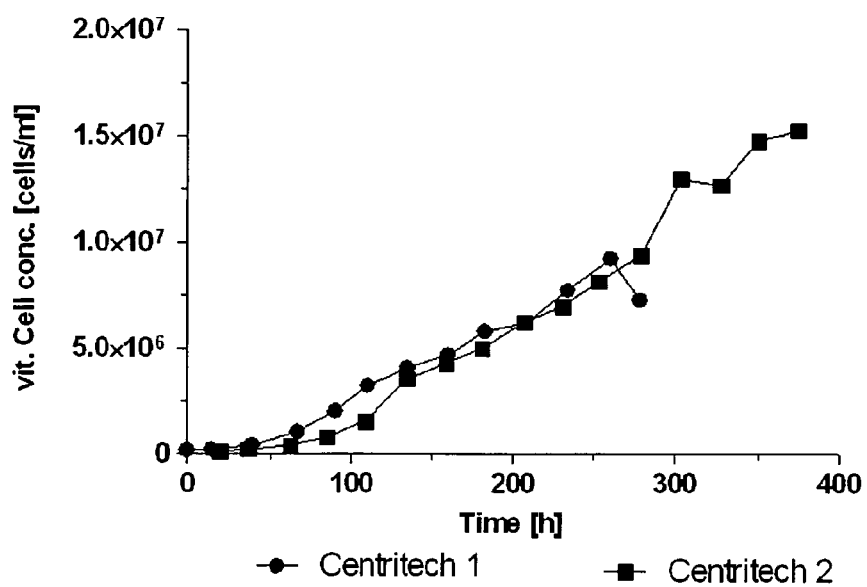
FIG. 2 shows a comparison of cell growth (A), spec. productivity (B), viability (C), perfusion rates (D) and glucose concentration (E) for two comparable perfusion runs using Centritech Lab II for cell retention of GlycoExpress A hPM in continuous mode.
Figure 2:
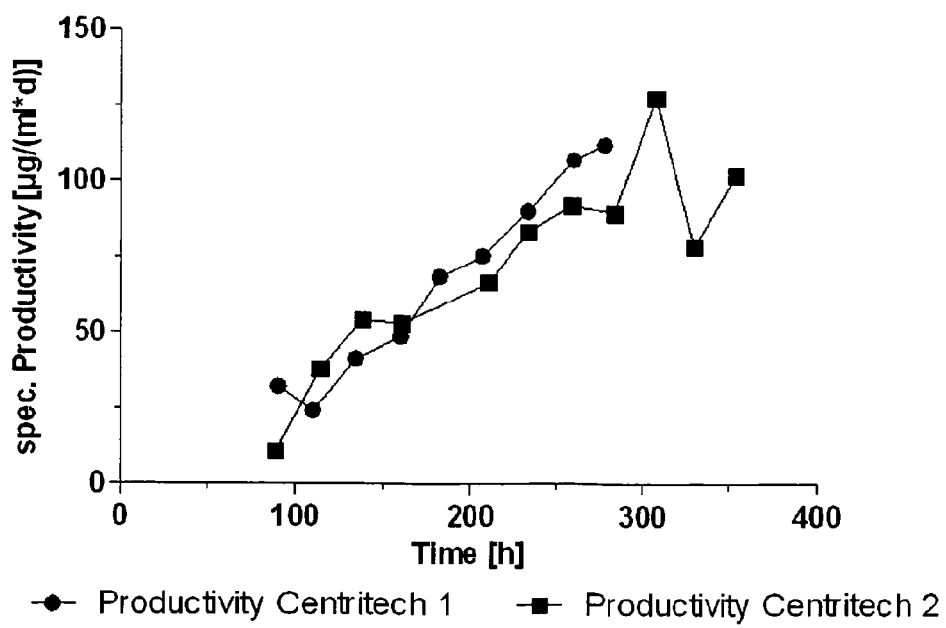

Using the Centritech Lab Centrifuge, cells grew at very high viability, and cell densities of above $10*10^6$ cells/ml were achieved. The results (see FIG. 2) proved to be highly reproducible and no inhomogeneities regarding product glycosylation (GlycoExpress A hPM) were found. The processes were run for at least 300 h of cultivation time. The specific productivity reaches a maximum of about 100 μg/(ml*d) at a perfusion rate of two bioreactor volumes per day. The average specific productivity was at about 70 μg/(ml*d) for lab scale fermentation scale.

A preferred perfusion process is shown in Table 2.

TABLE 2

Preferred perfusion process

| Parameter | Setpoint & Remarks |
|---|---|
| pH | 7.2; $CO_2$/NaOH; deadband +/− 0.1 units |
| DOT | 40% air saturation, four gas ($N_2$, $CO_2$, air, $O_2$); gas mix |
| Temperature | 37° C. |
| Perfusion rate | 0.5-2.5 V/d |
| Cell retention | Centritech, continuous centrifuge, pump mode |
| Agitation | 3 blade pitched impeller |
| Spec. Power Input | 0.022 W/m³ without baffles |

13.2 Confirmation of Product Quality in Continuous Fermentation

As already seen in batch fermentations, the product quality is remarkably robust. The product was biochemically analyzed. Regarding multimers, there is a portion of 3% non-monomeric antibody, which is comparable to the batch fermentation. The antigen ELISA complies within the specification as it shows high specific binding. Additionally, the glycosylation pattern of GlycoExpress A hPM is similar in two independent performed perfusion runs, but also in comparison to the spinner/batch produced product.

In SDS-PAGE (reducing conditions), there were clear bands for the separate light- and heavy antibody chain. Heavy chain (=50 kDa) and light chain (=25 kDa) show sizes as expected.

13.3 Glycosylation During Perfusion

As product glycosylation may be affected by e.g. changes in media, mechanical stress or dissolved oxygen tension, during fermentation it becomes very important to analyze the development of the glycosylation pattern. With regard to process robustness, product glycosylation is one of the most important parameters to be analyzed.

Product glycosylation of the GlycoExpress cell lines was analyzed for a perfusion run which is performed at 3° C., 40% DOT, pH 7.2 with GT K4-Medio using GlycoExpress B. The product was analyzed for samples taken between day 3 and day 20 of the perfusion process. Despite some variations, the glycosylation pattern can be regarded as stable.

Concluding, there is no variation in glycosylation during the process. With regard to process robustness and cell line robustness the fermentation provides stable product glycosylation. The perfusion fermentation of GlycoExpress A hPM results in a highly pure, biochemical active product.

13.4. Conclusion

A perfusion process for GlycoExpress cell lines features high cell viability during high density fermentation. The perfusion process features a constant product quality and especially a constant glycosylation pattern. The fermentation process is controlled at pH 7.2; DOT 40% and at a temperature of 37° C. Ferme ntation with GlycoExpress cells can be performed with a high power input (0.022 W/m³), as cells tolerate high shear forces.

Example 14

Comparison of Different Production Methods

Regarding biochemical product quality, all processes (spinner, batch, fed-batch (data not shown) and perfusion) provided similar highly monomeric, bioactive antibody. Analysis using size-exclusion chromatography (SEC) resulted in a portion of 2-3% of multimeric antibody. While batch and fed-batch fermentation product showed about 2% multimers, perfusion showed about 3% of multimer, which is still comparable to the spinner product. A multimer portion of 2-3% can be easily removed during downstream processing (DSP), for GlycoExpress A hPM a multimodal anion exchange column is applied. During this step of DSP also host cell protein (hcp) and human serum albumin (HSA) are depleted. Additional analysis in SDS-PAGE showed comparable protein purity for all processes. Product was analyzed under non-reducing conditions (whole antibody structure) and under reducing conditions (separation of heavy and light chain). Identity of antibody chains was confirmed using Western blot. Regarding bioactivity all samples are analyzed in an antigen binding ELISA. Samples show high binding to glycosylated MUC1-peptide and very little binding to non-glycosylated MUC1 peptide, which was in agreement with the specification for all processes.

As one of the most important features, antibody glycosylation was analyzed for spinner, batch, fed-batch and perfusion culture. The glycosylation pattern was very homogeneous. Due to the complexity of glycoprofiling (see also section 4.5.4) a standard deviation of +/−4% is measured. Therefore, only changes in glycosylation >5% are considered significant.

Summarizing, the glycosylation pattern is very robust. It does not change in comparison to a low-agitated and non-aerated spinner cultures. Additionally it does not seem to be significantly sensitive to cell concentrations or cell viability as batch, fed-batches and perfusion processes differ in those properties (perfusion shows higher cell concentrations, fed-batch shows lower viabilities at harvest). As product quality is high for all batch, fed-batch and perfusion, the choice for the production process can be made based upon productivity and economic consideration as focus is put on development of a GMP-suitable process.

Example 15

Scale Up

It was found that the upstream processing scale up (>1000-fold) from spinner culture to a GMP production process provides up to 90 g of purified antibody without altering the product quality and especially the glycosylation profile.

Fermentation was performed in different scales. For the smallest scale (working volume 0.6 l) a DASGIP parallel bioreactor system was used. Cultures in 1 l and 10 l working volume scale are performed in Sartorius glass bioreactors (B-DCU 2 l, B-DCU 5 l) and a Sartorius stainless steel reactor (C-DCU 10 l). Additionally, a 10 l Applikon glass bioreactor was used. The largest scale (100 l) was carried out in a 100 l Applikon stainless steel fermenter. Accordingly, fermentations were not only done in four different scales, but also in fermenters of three different companies. A total scale up of factor 166 was done, using the following steps: 1:1.5:16:166. As fermenters of different companies are used for fermentation, which show different characteristics regarding geometric properties, aeration and agitation, scale up becomes even more critical.

15.1 Scale Up Conditions

When performing scale up, cells have to be especially robust with regard to shear forces. Since cells do not suffer damage by shear forces when using 400 rpm in a 2 l Sartorius vessel, power input was chosen to be scale up criterion as cells appear to be highly shear force resistant. Consequently, the specific power input (power input per volume) is selected to be constant in all different fermenter sizes. Once power input is chosen as scale up criterion, a specific power input of about Pspec=0.02 W/kg is selected. This equals a stirrer speed of 300 rpm in a Sartorius 2 l fermenter. This stirrer speed shows excellent mixing and homogenization properties.

Although geometric similarity is normally an important pre-condition for scale up, successful upscaling can be performed in highly diverse vessels. Table 6 shows results of successful upscaling using power input as criteria. Besides the Applikon 10 l Fermenter, all fermenters can support a similar specific power input. It should be noted, that both Applikon fermenters use the maximal possible stirring speed (rpm). Therefore, it is not possible to operate the Applikon 10 l at same specific power input rates as the other fermenters.

TABLE 3

Geometric properties of employed fermentation vessels. Stirrer agitation [rpm] based upon constant power input for most common working volume.

|  | DASGIP 0.6 l | B-DCU 1 l | B-DCU 5 l | C-DCU 10 l | Applikon 10 l | Applikon 100 l |
|---|---|---|---|---|---|---|
| $D_t$ [m] | 0.125 | 0.130 | 0.160 | 0.215 | 0.222 | 0.491 |
| $D_i$ [m] | 0.055 | 0.034 | 0.070 | 0.110 | 0.074 | 0.234 |
| Angle | +30° | +30° | +30° | +30° | −45° | −45° |
| rpm [1/min] | 250 | 300 | 300 | 200 | 200 | 125 |
| Volume [l] | 2 | 3 | 5 | 15 | 15 | 130 |
| Max Volume [l] | 1.5 | 2 | 5 | 10 | 10 | 100 |
| Min Volume [l] | 0.4 | 0.6 | 1 | 4 | 4 | 30 |
| Working Volume [l] | 0.6 | 1 | 5 | 10 | 10 | 100 |
| Number of Stirrers | 1 | 1 | 2 | 2 | 1 | 1 |
| H [m] | 0.210 | 0.170 | 0.255 | 0.315 | 0.245 | 0.593 |
| $H_t$ [m] | 0.175 | 0.13 | 0.08 | 0.155 | 0.21 | 0.393 |
| $H_i$ [m] |  |  | 0.13 | 0.11 |  |  |
| $H_b$ [m] | 0.035 | 0.04 | 0.045 | 0.05 | 0.035 | 0.2 |
| $D_i/D_t$ | 0.44 | 0.42 | 0.44 | 0.51 | 0.33 | 0.48 |
| $H/D_i$ | 3.82 | 3.15 | 3.64 | 2.86 | 3.31 | 2.53 |
| $H/H_t$ | 1.68 | 1.31 | 1.59 | 1.47 | 1.10 | 1.21 |

Legend:

$D_i$: stirrer diameter; $D_t$: fermenter diameter; H: fermenter height; $H_t$: distance of upper stirrer to liquid surface; Hi: distance between stirrers; $H_b$: distance below lower stirrer.

As power input is kept constant during scale up (except for Applikon 10 l due to design limitations), shear forces increase during scale up. Calculated shear forces [N/m$^2$] are shown in table 4. The maximum shear forces are calculated for the stirrer tip, as this area is regarded as region of highest energy dissipation As cell growth seems not to be affected and viability does not drop with increasing reactor scales, GlycoExpress A hPM cells is shear resistant to at least 0.9 N/m$^2$ of permanent stirrer induced shear stress. This equals an at least 10-fold increase of shear resistance as compared to CHO cells, which take damage at shear rates of 0.1N/m$^2$ [Motobu et al. 1998].

TABLE 4

Result of scale up for different fermenters showing shear and mixing properties. Calculations are performed for bioreactor setup as shown in Table 6.

|  | DASGIP 1 l | B-DCU 1 l | B-DCU 5 l | C-DCU 10 l | Applikon 10 l | Applikon 100 l |
|---|---|---|---|---|---|---|
| Spec. Power Input [W/kg] | 0.021 | 0.020 | 0.023 | 0.021 | 0.003 | 0.022 |
| Tip Speed [m/s] | 0.72 | 0.85 | 1.10 | 1.15 | 0.77 | 1.53 |
| Tip Shear Rate [1/s] | 457 | 492 | 637 | 818 | 550 | 1375 |
| Mixing Time [s] | 2.87 | 2.77 | 2.43 | 2.43 | 7.32 | 4.67 |
| Circulation Time [s] | 1.05 | 0.99 | 0.89 | 0.97 | 2.30 | 1.80 |
| Shear force [N/m$^2$] | 0.30 | 0.32 | 0.45 | 0.53 | 0.36 | 0.90 |
| Reynolds | 19184 | 22192 | 37291 | 61390 | 27783 | 173630 |

15.2 Comparison of Different Scales

Figure 3:
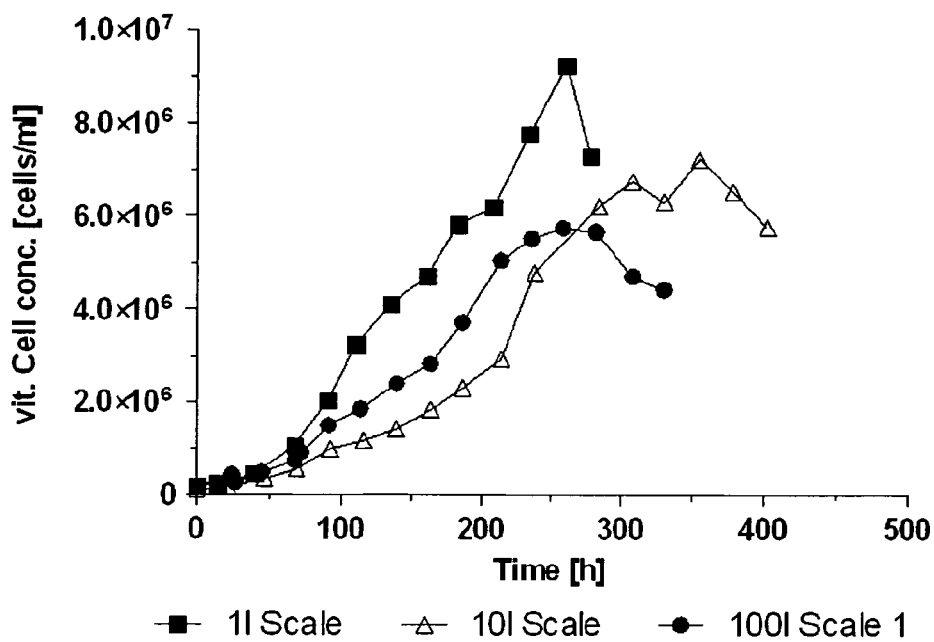
FIG. 3 shows exemplary data for scale up fermentations in 1 l; 10 l and 100 l scale. Cell growth (A), spec. productivity (B), viability (C), perfusion rates (D) and glucose concentration (E) for three fermentations under similar conditions using GlycoExpress A hPM are shown.
Figure 3:
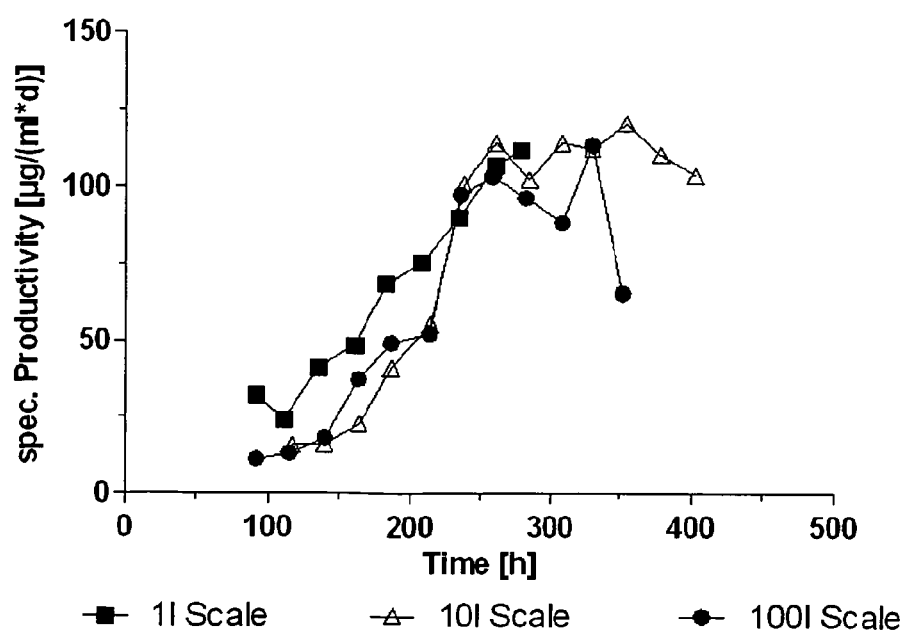

Scale up of perfusion fermentations has been performed using fermentation in 1 liter, 10 liter and 100 liter scale. FIG. 3 shows exemplary results for three similar fermentations of GlycoExpress A hPM controlled at 37° C., pH 7.2 and a DOT of 40%. Fermentation is performed in perfusion applying a similar feeding strategy as shown in FIG. 3 (D). Perfusion rates are set depending on the glucose consumption.

There are several differences between the lab scale process and the 100 l production scale regarding growth and productivity. Compared to a smaller scale fermentation (1 l working volume) where maximal cell concentrations of >10*10$^6$ cells/ml are achieved, cells do not grow to higher concentrations than 6*10$^6$ cells/ml in 10 l and 100 l perfusion. Following, there is less glucose consumption with increasing scale and glucose concentration is kept at above 1.5 g/l for the 100 l scale. In small scale fermentations where cells usually grow to higher concentrations, glucose is consumed to concentrations of below 1 g/l.

In contrast to different viabilities and viable cell concentrations, there is almost the same level of productivity in all scales. All fermentations have a peak productivity of >100 µg/(mld) and also show a very comparable productivity curve.

Summing up, the scale up provides a process which is capable of producing large amounts of product. Product concentrations are similar in all scales. The maximal productivity is at >100 µg/(mld). There is, however, a significant decrease in viability and maximal cell concentration to be recognized in increasing scale. Regarding maximal cell concentration the cell retention of the centrifuge has a significant effect. While being >99% in lab scale, it drops to ca. 90% in production scales. This results in a constant bleeding which leads to a reduction of the maximal cell concentration.

15.3 Large Scale Perfusion

Figure 4:
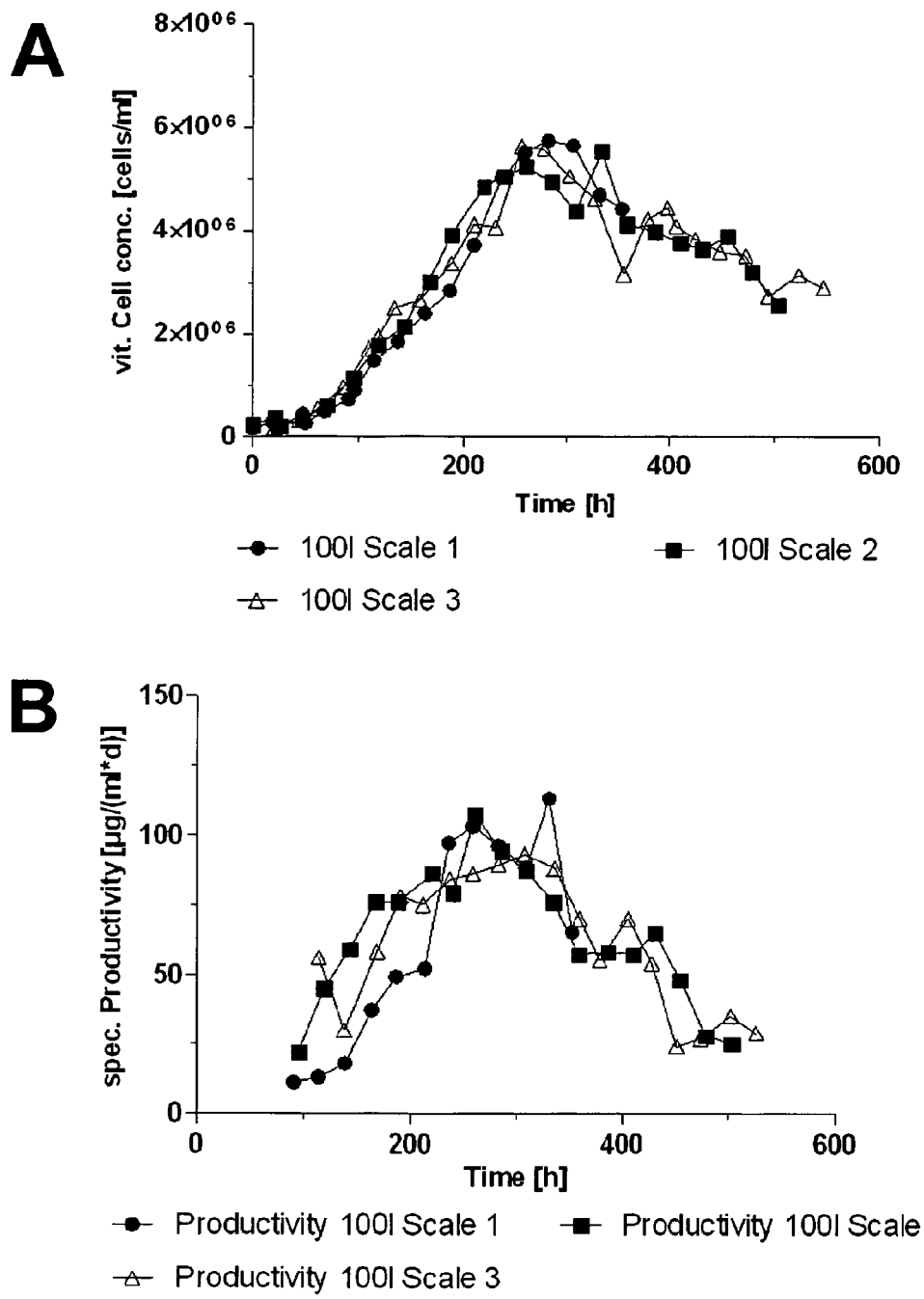
FIG. 4 shows a comparison of similar 100 l perfusion runs. Cell growth (A), spec. productivity (B), viability (C), perfusion rates (D) and glucose concentration (E) for three replicate fermentations are shown.

Large scale perfusion runs are carried out in an Applikon 100 l fermenter. Using perfusion, up to 250 l media/day are used when operating at 100 l working volume. FIG. 4 shows results for three comparable 100 l perfusion runs, which are performed under GMP conditions. Those fermentations are highly reproducible. All fermentations have been performed using the established perfusion process conditions (see above). All three fermentations show similar behaviour concerning productivity and cell growth. The maximal cell concentration peaks at 6*10$^6$ cells/ml and drops significantly afterwards. In late stage of perfusion cell densities of about 3-4*10$^6$ cells/ml are obtained. Consequently, as cell growth is closely linked to productivity, there is also a maximum at specific productivity. Specific productivity peaks at about 100 µg/(ml*d). During late stage, specific productivity drops to <40 µg/(ml*d). Concerning viability, the fermentations are started at >90% but drop to about 80% upon start of perfusion.

The glycosylation pattern was constant for all three fermentations within measurement fluctuations.

15.4 Conclusion Scale Up

Scale up has been applied to the perfusion process using the Centritech continuous centrifuge. Fermentation equipment provides certain limitations, e.g. different bioreactor types using different aeration setups, different geometric properties, limitations in agitation (speed, number of stirrers). As cells prove to be highly shear force resistant, the power input is used as scale-up criteria. This results in increasing stirrer induced shear forces with increasing fermenter size but provides sufficient mixing in lab scale. Nonetheless, scale up resulted in highly viable high density cultures with constant product glycosylation. Product quality (measured by SEC, bioassay, glycoprofile) is generally unaltered by scaling up. Fermentations are successfully realized for the production of up to 90 g of antibody (amount before downstream processing). It has been demonstrated through the qualitative and the quantitative performance evaluation of the 1 l, 10 l and 100 l bioreactors, as well as through a panel of biochemical characterization tests, that the comparability of the process and the product was well maintained during the process of scale up.

Example 16

Culture Media

Cells were cultured in suspension using different media. Mainly used media are: x-Vivo20 (Lonza, Belgium), GTM-1 (Biochrom, Germany), GTM-2 (Biochrom, Germany), GTM-3 (Biochrom, Germany), GTM-4 (Biochrom, Germany), GTM-5 (Biochrom, Germany), GTM-6 (Biochrom, Germany), GTM-7 (Biochrom, Germany), GTM-8 (Biochrom, Germany) and GTM Feed Medium (Biochrom, Germany). Media are based upon a basal medium, with has been supplemented with additional nutrients. General nomenclature of GTM media is given in Table 6.

TABLE 6

Overview of GTM media

| Name | Remark |
|---|---|
| GTM-1 | Basal powder media with further additives |
| GTM-2 | As GTM1 with reduced osmolarity due to lower glucose 4.5 g/l |
| GTM-3 | Research media as GTM-2 w/o Gle/Gln/HSA |
| GTM-4 | Low HSA media (0.002%), remaining composition as GTM-2 |
| GTM-5 | As GTM2, single component based. |
| GTM-6 | Low HSA media (0.002%), remaining composition as GTM-5 |
| GTM-7 | Lipid-free media based upon GTM-5 |
| GTM-8 | Low HSA media (0.002%), remaining composition as GTM-7 |

As discussed above, the power input is preferably used as scale up criterion. The subsequent equation shows basic formula for power input (P) calculation dependent on stirrer speed (N), stirrer diameter (di), media density (p) and a stirrer constant (Ne).

$$P = N_e \rho N^3 d_i^5$$

Theoretically, stirrer speed during scale up can be kept constant, if the impeller diameter to vessel diameter ratio (di=dt) is kept constant. Nevertheless, this is in most cases not possible due to bioreactor vessel dimensions. In order to correlate the power input to fermentation volume, specific power input (Pspec) can be calculated. Specific power input is a commonly used scale up criterium. In order to apply it to a process, cells must be rather insensitive to shear forces, which increase with bioreactor volume (V). The subsequent equation shows calculation of specific power input.

$$P_{spec} = \frac{P}{V}$$

The tip speed increases linear with stirrer diameter and stirring speed. Therefore a constant tip speed ($v_{Tip}$) results in a decrease of rounds per minute (rpm) in a large vessel. This is directly dependent on larger stirrer diameters in large vessels. Possibly, there is no sufficient power input which can result in poor mixing or even cell sedimentation. Consequently, scaling up with constant stirrer tip shear rate can only be applied to extremely shear sensitive cells. The subsequent equation shows calculation for stirrer tip velocity dependent on stirrer diameter and stirrer speed.

$$v_{Tip} = \pi d_i N$$

In a bioreactor, maximal shear forces arise at the outer side of the stirrer. Therefore, shear rate $$\gamma (|\gamma|=1/s)$$

should be calculated at the stirrer tip using the above formula. The shear rate is dependent on stirring speed (N), stirrer diameter (di) and the kinematic viscosity (v). In this work, the kinematic viscosity is assumed as constant even though high cell concentrations might increase it.

$$\gamma = 3.3 \left( \frac{Nd_i^2}{v} \right)^{0.5} N^1$$

Using stirrer tip shear rate as scale up criteria will result in decreasing agitation speed (rpm) with increasing fermenter size. As mentioned before, poor mixing or even cell sedimentation can occur. Consequently, scaling up with constant stirrer tip shear rate is preferred with extremely shear sensitive cells. The cells that used according to the present invention are shear resistant.

The invention claimed is:

1. A method for culturing a suspension of immortalized human blood cells in cell culture medium, wherein
   said suspension is agitated such that the resulting specific power input is at least 0.005 W/kg.

2. The method of claim 1, wherein the specific power input for agitation of the suspension is at least 0.01 W/kg and a gas supply is achieved by exclusive gas flow.

3. The method according to claim 2, wherein the peak gas flow is 0.05 vvm or less.

4. A method for the recombinant production of a product of interest in immortalized human blood cells, wherein said cells comprise a gene encoding the product of interest and wherein said cells are cultured according to the method of claim 1.

5. The method according to claim 4, wherein the expressed product of interest is obtained by purifying the product of interest from the cell culture medium.

6. The method of claim 1, wherein the immortalized human blood cells are human myeloid leukaemia cells.

7. The method of claim 1, wherein the cells are cultured by continuous fermentation with cell retention.

8. The method of claim 7, wherein a continuous centrifuge is used for cultivation.

9. The method of claim 1, wherein cells are removed during cultivation.

10. The method of claim 1, wherein the cells in the cell culture reach a density of at least $1 \times 10^6$/ml.

11. The method of claim 1, wherein cell viability in the cell culture is at least 70%.

12. The method of claim 1, wherein fermentation has a peak productivity of at least 80 μg/(mld).

13. The method of claim 1, wherein a stirrer is used for agitation.

14. The method of claim 1, wherein said method has one or more of the following further characteristics:
   a) said suspension is agitated with an intensity that is suitable for allowing an exclusive flow gas supply of said suspension,
   b) said suspension is agitated such that the resulting shear force is at least 0.1 N/m²,
   c) said suspension is agitated such that the resulting shear rate at the tip of the stirrer is at least 300 s⁻¹, if a stirrer is used for agitation,
   d) said cells are supplied with at least one gas by exclusive flow,
   e) said cells are supplied with at least one gas at a flow rate of at most 0.05 l/h per liter of reactor volume, and/or
   f) a gas supply has a peak flow rate of 0.05 vvm or less.

15. The method of claim 14, wherein pulses of at least one gas are used for aeration or pure oxygen is supplied.

16. The method of claim 14, wherein bubbles are produced by aeration which have a size of >5 mm.

17. The method of claim 14, wherein a device selected from the group consisting of a ring sparger, a micro sparger and a membrane is used for aeration.

18. The method of claim 14, wherein an oxygen value in the cell culture is determined and wherein oxygen and/or an oxygen containing gas or gas mixture is introduced as a pulse into the cell culture medium if the oxygen value drops below a predetermined level.

19. The method of claim 1, wherein a base is added during cultivation to maintain a predetermined pH level or range.

20. The method of claim 1, wherein a fermenter which has a volume of at least 1 l to 1000 l is used to culture the cells.

21. The method of claim 1, wherein the cell culture medium comprises a shear protective agent or the cells are cultured in a serum-free medium.

22. A method for upscaling the culture process of claim 1, wherein power input is used as scale up criteria.

23. The method of claim 1, wherein cell cultivation is performed at a pH range between 6.5 and 8; a $pO_2$ of 30% to 50%, and/or a temperature of 30 to 40° C.

24. The method of claim 4, wherein the product of interest is a glycoprotein.

25. The method of claim 24, wherein the glycosylation structure of the glycoprotein of interest or cell production rate is substantially unaffected by culture volume.

26. The method of claim 6, wherein the cells are K562 cells or cells derived therefrom.

\* \* \* \* \*